US007999541B2

(12) United States Patent
Chisholm et al.

(10) Patent No.: US 7,999,541 B2
(45) Date of Patent: Aug. 16, 2011

(54) SYSTEM AND METHOD FOR IMPROVING THE ANALYSIS OF POLYMORPHIC CHEMICAL SUBSTANCE FORMS AND CONCENTRATIONS USING NQR

(75) Inventors: Warrick Paul Chisholm, Northampton (AU); Laurence Drew Mann, Bateman (AU); Timothy Rayner, Crawley Down (GB); John Alec Sidney Smith, London (GB)

(73) Assignee: Rapiscan Security Products, Inc., Torrance, CA (US)

( * ) Notice: Subject to any disclaimer, the term of this patent is extended or adjusted under 35 U.S.C. 154(b) by 468 days.

(21) Appl. No.: 11/914,513

(22) PCT Filed: May 16, 2006

(86) PCT No.: PCT/AU2006/000651
§ 371 (c)(1),
(2), (4) Date: Aug. 5, 2008

(87) PCT Pub. No.: WO2006/122355
PCT Pub. Date: Nov. 23, 2006

(65) Prior Publication Data
US 2008/0309339 A1    Dec. 18, 2008

(30) Foreign Application Priority Data

May 16, 2005    (AU) .................................. 2005902468

(51) Int. Cl.
*G01V 3/00*    (2006.01)
(52) U.S. Cl. ........................ 324/300; 324/307; 324/309
(58) Field of Classification Search .......... 324/300–322; 600/410–435; 382/128–131
See application file for complete search history.

(56) References Cited

U.S. PATENT DOCUMENTS

| 5,592,083 | A | 1/1997 | Magnuson et al. |
| 5,608,321 | A | 3/1997 | Garroway et al. |
| 6,291,994 | B1 | 9/2001 | Kim et al. |

(Continued)

FOREIGN PATENT DOCUMENTS

EP    1 416 291 A2    5/2004
(Continued)

OTHER PUBLICATIONS

Balchin, E; Malcolme-Lawes, D.J; Poplett, I.J.F; Smith, M.J.A.S; Pearce, G.E.S; Wren, S.A.C, Potential of Nuclear Quadrupole Resonance Pharmaceutical Analysis, Analytical Chemistry, 2005, 77, 3925-3930.

(Continued)

*Primary Examiner* — Brij B. Shrivastav
*Assistant Examiner* — Tiffany A Fetzner
(74) *Attorney, Agent, or Firm* — Novel IP

(57) ABSTRACT

A method for analysing a chemical substance containing quadrupolar nuclei to determine a measurable characteristic of the substance. The method includes irradiating the substance with RF energy in a prescribed manner to stimulate NQR of certain quadrupolar nuclei within the substance. Then receiving and processing a signal emitted from the substance to isolate an NQR signal therefrom. Thereafter analysing the NQR signal to obtain a measure of the characteristic of the substance; and providing an output indicative of the measure for analytical purposes. Specific methods for analysing a chemical substance during production thereof to determine a characteristic of the substance indicative of the quality thereof, and for searching for chemicals together with specific systems are also described.

28 Claims, 25 Drawing Sheets

U.S. PATENT DOCUMENTS

| | | | |
|---|---|---|---|
| 6,566,873 B1 * | 5/2003 | Smith et al. | 324/300 |
| 7,109,705 B2 * | 9/2006 | Smith et al. | 324/300 |
| 2005/0073306 A1 * | 4/2005 | Smith et al. | 324/316 |
| 2006/0273786 A1 * | 12/2006 | Smith et al. | 324/300 |
| 2008/0309339 A1 * | 12/2008 | Chisholm et al. | 324/315 |

FOREIGN PATENT DOCUMENTS

| | | |
|---|---|---|
| GB | 2284898 A * | 6/1995 |
| WO | WO 04/001454 A1 | 12/2003 |
| WO | WO 2005/001451 A2 | 1/2005 |
| WO | WO 2006/084313 A1 | 8/2006 |

OTHER PUBLICATIONS

Perez, S.C; Cerioni, L; Wolfenson, A.E; Faudone, S; Cuffini, S.L, Utilization of Pure Nuclear Quadrupole Resonance Spectroscopy for the Study of Pharmaceutical Crystal Forms, International Journal of Pharmaceutics, 2005, 298,143-152.

Brame, E.G, Analytical Aspects of Nuclear Quadrupole Resonance Spectroscopy, Analytical Chemistry, 1967, 39, 918-921.

Yesinowski, J.D; Buess, M.L; Garroway, A.N, Detection of 14N and 35Cl in Cocaine Base and Hydrochloride Using NQR, NMR, and SQUID Techniques, Analytical Chemistry, 1995, 67, 2256-2263.

Anferov, VP; Anferova, S.V; Grechishkin, V.S; Sinjaysky, N.J, Method of Adiabatic Demagnetisation in NQR, Journal of Molecular Structure, 1982, 83,89-92.

Hirschfeld, T; Klainer, S.M, Short Range NQR Measurements, Journal of Molecular Structure, 1980, 58, 63-77.

Latosinska, J.L, Applications of Nuclear Quadrupole Resonance in Drug Development, Expert Opinion in Drug Discovery 2, 2007, 2, 225-248.

Garroway, A.N.,Nuclear Quadrupole Resonance (Paper II), in Alternatives for Landmine Detection,eds. J. Macdonald et at, Rand, Santa Monica, CA, 2003.

Thurber, K.R; Sauer, K.L; Buess, M.L; Klug, C.A; Miller, JB, Increasing 14N NQR Signal by 1H—14N Level Crossing by Small Magnetic Fields, Journal of Magnetic Resonance, 2005, 177,118-128.

Thayer, A.M; Millar, J.M; Pines, A., Two Dimensional Zero Field NMR and NQR, Chemical Physics Letters, 1986, 129(1),55-58.

Miller, J.B; Barrall, G.A, Explosives Detection with Nuclear Quadrupole Resonance, American Scientist, 2005, 93(1); 50.

Somasundaram, S; Jakobsson, A; Smith, J.A.S, Frequency Selective Detection of NQR Signals in the Presence of Multiple Polymorphic Forms, 14 European Signal Processing Conference, Sep. 2006.

Schultz, H.D; Karr, C, Quantitative Aspects of Nuclear Quadrupole Resonance Spectrometry of Inorganics and Minerals, Analytical Chemistry, 1969, 41, 661-664.

Hacobian, S, Evaluation of the Effect of Some Experimental Parameters in the Determination of Chlorine Nuclear Quadrupole Resonance Spectra, Australian Journal of Chemistry, 1962, 15, 21-33.

Alexander, S; Tzalmona, A, Relaxation by Slow Motional Processes. Effect of Molecular Roatations in Pure Quadrupole Resonance, Physics Review, 1965, 138, A845-A855.

Ivanov, D; Redfield, A.G, Field-Cycling Method With Central Transition Readout for Pure Quadrupole Resonance Detection in Dilute Systems, Journal of Magnetic Resonance, 2004, 166, 19-27.

Bavin, P.M.G; Stephenson, D; Smith, J.A.S, 14N Quadrupole Cross-Relaxation Spectroscopy of a Compound of Pharmacological Interest, Zeitschrift fur Naturforschung, 1986, 41a, 195-199.

Bussandri, A.P; Zuriaga, M.J, Spin-Echo Mapping Spectroscopy Applied to NQR, Journal of Magnetic Resonance, 131, 224-231.

Blanz, M; Rayner, T.J; Smith, J.A.S, A Fast Field-Cycling NMR/NQR Spectrometer, Measurement Science and Technology, 1993, 4, 48-59.

Blinc, R; Seliger, J; Zidansek, A; Zagar, V; Milia, F; Roberts, H, 14N Nuclear Quadrupole Resonance of Some Sulfa Drugs. Solid State NMR, 2006, 30, 61-68.

Grechishkin, VS; Ya Sinyayskii, N, New Technologies: Nuclear Quadrupole Resonance as an Explosive and Narcotic Detection Technique, Physics Uspekhi, 1997, 40, 393-406.

Liao, M,Y; Harbison, GS, Condensed Phase Dynamics, Structure, and Thermodynamics: Spectroscopy, Reactions and Relaxation—Two-Dimensional Nuclear Magnetic Resonance Correlation Spectroscopy at Zero Field, Journal of Chemical Physics, 1999, 111, 3077-3082.

No Author, (Dec. 29, 2004) "Hands Off! NMR Drives Non-Contact Check Weighing System", downloaded from http://www.pharmamanufacturing.com/industrynews/2004/17.html.

No Author, (Jul. 2001) "New on-line analyser for quality measurement of butter", downloaded from http://www.apv.com/us/enc/newsandevents/foodanddrink/iu1v2001/New+online+analyser+for+quality+measurement+of+butter.htm.

International Search Report Dated Jun. 28, 2006.

* cited by examiner

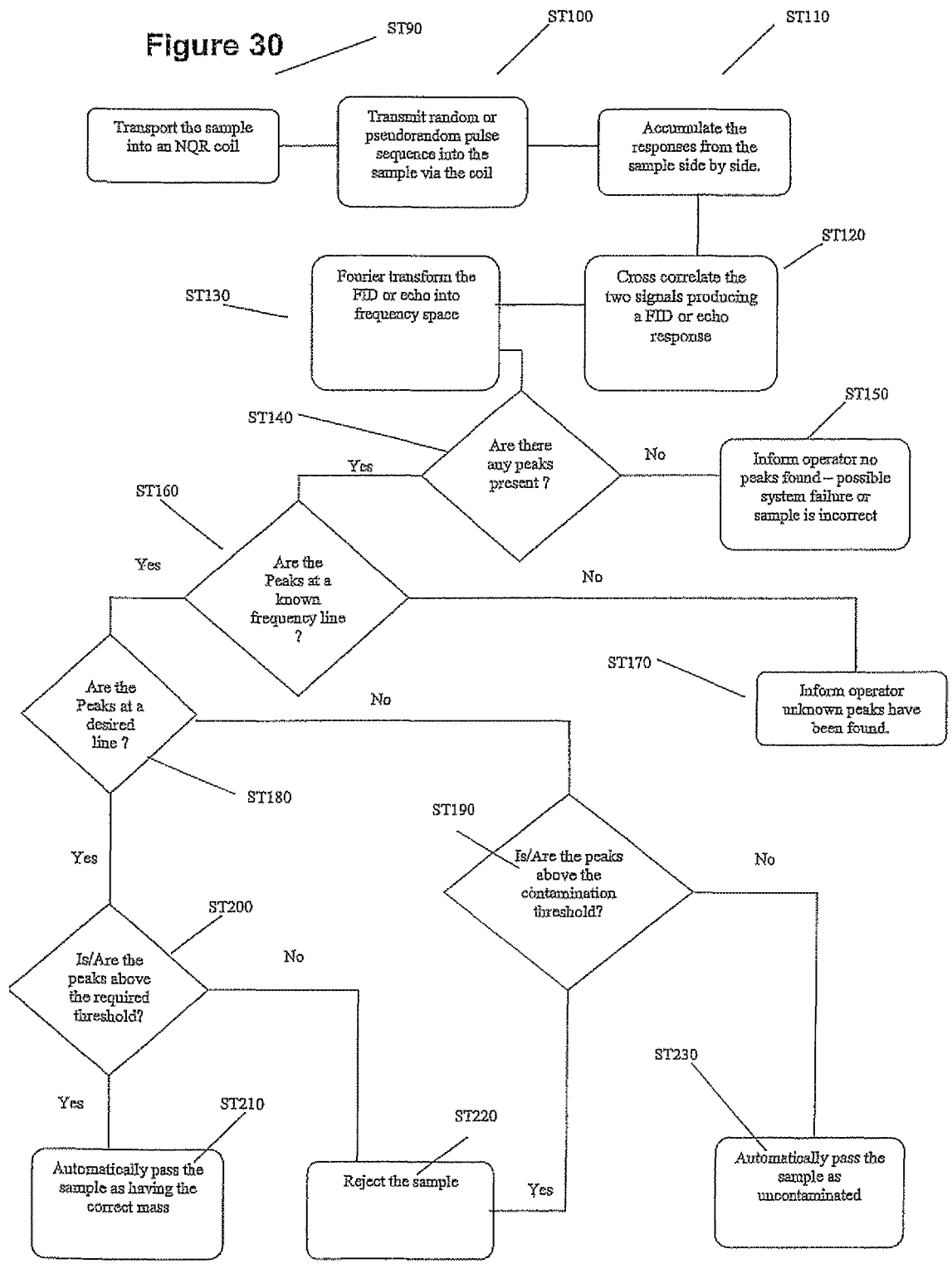

SYSTEM AND METHOD FOR IMPROVING THE ANALYSIS OF POLYMORPHIC CHEMICAL SUBSTANCE FORMS AND CONCENTRATIONS USING NQR

FIELD OF THE INVENTION

This invention relates to the analysis of chemical substances. The invention has particular, although not exclusive, utility with respect to the quality control of mass-produced chemical substances.

These chemical substances may be in a variety of forms or applications. For example, they be in the form of pharmaceuticals or medicines, cosmetics, health, beauty or safety products such as vitamin preparations, ointments and cremes, fertilizers, textiles, agricultural and mining products, foodstuffs, plastics and indeed, any other manufactured product where it is desirable to exercise some form of analysis or quality control over the make-up of the chemical composition, and where the input, intermediary or output form of the composition or product is a solid and contains quadrupolar nuclei.

Throughout the specification, unless the context requires otherwise, the word "comprise" or variations such as "comprises" or "comprising", will be understood to imply the inclusion of a stated integer or group of integers but not the exclusion of any other integer or group of integers.

The term "in-line" refers to an operation that is performed concurrently and repetitively as part of a production stage of the manufacturing process.

The term "off-line" refers to an operation that is performed separately and remotely of a production stage of the manufacturing process.

BACKGROUND ART

Organic chemical analysis is a key part of the identification, development, and quality assurance of new pharmaceuticals. For example analytical methods play a critical role in supporting the scaling up of the synthetic route; development of the manufacture of the final dosage form; assessment of stability; and control of quality and consistency of the commercial product.

One of the problems with existing techniques used for the analysis of chemical substances is the speed and quality of decision-making. There is a need for products and processes to be characterised more quickly and more fully, with the ultimate aim of decreasing development times, reducing manufacturing costs, and increasing the quality and safety of the final product.

Another problem is that most pharmaceuticals are marketed as solid dosage forms, for example oral tablets, but the majority of the organic chemical analysis techniques used are solution based. Some examples of analytical techniques of this nature that are widely used in assessing the quantity of active agent, chemical purity, and the identification of both active agent and impurities are HPLC (high pressure liquid chromatography), electro-spray MS (mass spectrometry), and solution NMR (nuclear magnetic resonance). Whilst such techniques enable tight control of the quality and consistency of the dosage form of a pharmaceutical, they inevitably require time and effort in sample preparation and are inherently destructive in nature.

Other important information, such as the polymorphic form of the active agent, is lost by solution-based methods and so solid-state techniques are required to be used in an attempt to attain such information. Examples of some solid-state analytical techniques that have been developed include IR (infra-red), powder XRD (x-ray diffraction), and solid state NMR. Problems with these techniques, however, include:
  they are performed off-line;
  they require the sample to be removed from any packaging;
  they are slow, time intensive, expensive techniques—some NMR analyses can take 24 hours;
  near IR techniques require a significant calibration step;
  a NMR requires a large bulky magnet which can be dangerous if it has a high field strength, because metallic objects can be launched by its magnetic field;
  NMR spectra are difficult to interpret because of many overlapping lines;
  NMR & XRD are generally very expensive machines.

The problem with off-line pharmaceutical analysis is that it is usually conducted remotely of the process sought to be controlled by the results of the analysis. Most control strategies rely on end point testing in which the manufactured material is sampled and the samples brought to the laboratory for testing. End point testing imposes limits on the timescale in which process changes can be made.

Techniques such as Near IR (NIR) have evolved that provide for in-line testing, but as NIR is a secondary technique, a significant calibration exercise is required before data can be interpreted in a meaningful way.

NQR is a technique in radiofrequency (RF) spectroscopy in which the signals arise from the interaction of the electric quadrupole moment of the quadrupolar nuclei in the sample with the electric field gradient (EFG) of their surroundings. RF radiation excites transitions between the energy levels generated by this interaction at frequencies, which are characteristic of a given material.

Some of the characteristics of NQR are that the method of its deployment is generally non-invasive and that NQR signals are only seen in solids, but suspensions of solid materials within liquids are eligible for detection. Furthermore, it is relatively inexpensive to deploy. Unlike NMR, for example, no static magnetic field is necessary, so remote materials and large volumes—at the moment, the record is 8000 litres[2]— can be examined.

NQR has been mooted for many years as a technique that can be used for the detection of explosives and narcotics in the field, as opposed to the laboratory. Most of these substances contain quadrupolar nuclei such as nitrogen-14 ($^{14}$N) nuclei, the spectral lines of which are usually located at low frequencies where NQR signals detected have low intensity. In this application of NQR, specimens are sampled to ascertain the threshold presence of a targeted chemical substance indicating the presence of a particular type of explosive or narcotic.

A number of problems associated with deploying NQR in the field as a reliable and quick technique to ascertain the presence of the targeted substance have arisen, however, preventing the technique from being used more widely than it has to date. Some of these problems include what are known as intensity variations, where the amplitude of the resultant NQR signal strongly depends on the frequency offset and repetition time of the exciting RF radiation, and the effect of temperature on changing the frequency at which an NQR signal may be detected.

Notwithstanding these problems, processes have been developed in more recent times to overcome these problems, making NQR more reliable as a technique for detecting the presence of a substance. Moreover, it is the realisation that new developments in pulsed RF spectroscopy and new methods of improving the signal-to-noise ratio (SNR) now suggest the possibility of a much wider application of NQR techniques to chemical analysis, particularly at the low radiofrequencies typical of $^{14}N$, which was not previously the case.

DISCLOSURE OF THE INVENTION

It is an object of the present invention to provide for improved analysis of chemical substances that is non-invasive, non-destructive and fast compared with present commonly used techniques.

It is a preferred object of the invention to permit to either individual analysis of a chemical substance or 'in-line' analysis where the substance is mass-produced.

It is a particularly preferred object of the invention to provide for improved quality control of mass produced pharmaceuticals.

According to one aspect of the present invention, there is provided a method for analysing a chemical substance containing quadrupolar nuclei to determine a measurable characteristic of the substance, comprising:
irradiating the substance with RF energy in a prescribed manner to stimulate NQR of certain quadrupolar nuclei within the substance;
receiving and processing a signal emitted from said substance in close association with the irradiating to isolate an NQR signal therefrom;
analysing said NQR signal to obtain a measure of the characteristic of the substance; and
providing an output indicative of said measure for analytical purposes.

Preferably, the characteristic of the substance is concerned with ascertaining the amount of a certain chemical in the substance being analysed.

Preferably, the characteristic of the substance is concerned with ascertaining the purity of the substance.

Preferably, the characteristic of the substance is concerned with identifying the particular form of a certain chemical in the substance.

Preferably, the form is the particular polymorph of the chemical.

In accordance with another aspect of the present invention, there is provided a method for analysing a chemical substance during production thereof to determine a characteristic of the substance indicative of the quality thereof, comprising:
irradiating the substance with RF energy in a prescribed manner to stimulate NQR of certain nuclei within the substance;
receiving and processing a signal emitted from said substance in close association with the irradiating to isolate an NQR signal therefrom;
analysing said NQR signal to obtain an actual indication of the characteristic of the substance indicative of the quality thereof;
comparing said actual indication with prescribed reference parameters pertaining to that characteristic; and
providing an output signal indicative of the result of said comparison to signify whether the chemical substance is in accord with quality requirements prescribed for that characteristic.

Preferably, the method includes calibrating the analysing to take into account the existing environmental conditions that could influence the accuracy of the actual indication of the characteristic relative to the prescribed reference parameters.

Preferably, the calibrating includes measuring the temperature external of the substance.

Preferably, the calibrating includes measuring the actual temperature of the substance.

In accordance with another aspect of the present invention there is provided a system for analysing a chemical substance to determine a characteristic of the substance, comprising:
a chamber for receiving the chemical substance therein;
a probe to irradiate said chamber with RF energy;
generating and transmitting means to generate and transmit a signal in a prescribed manner to excite said probe so as to irradiate said chamber with RF energy specifically prescribed to stimulate NQR of certain nuclei within the substance;
receiving and processing means to receive signals from said chamber in close association with said signal to isolate an NQR signal therefrom; and
analysing means to analyse said NQR signal in a manner so as to obtain a measure of the characteristic of the substance.

Preferably, said signal is a phase-cycled multi-pulse sequence.

Preferably said signal is an extended time echo sequence.

In accordance with a further aspect of the present invention, there is provided a method for analysing a chemical substance to determine a characteristic of the substance related to the quality of production thereof, comprising:
(i) conveying a chemical substance into an analysing volume;
(ii) irradiating said analysing volume with RF radiation in accordance with a prescribed pulse sequence at a prescribed frequency;
(iii) receiving signals from said chemical substance at said prescribed frequency;
(iv) processing said signals for NQR signals;
(v) determining quadrupole parameters from said NQR signals including any one of: line-width, frequency, peak height, impurity frequency or peak height; or any combination of same;
(vi) determining the size of said quadrupole parameter(s);
(vii) comparing said size against reference parameter(s) to determine a qualitative measure of a characteristic of said substance determinative from said quadrupole parameters); and
(viii) signalling if said qualitative measure differs beyond a threshold amount from said reference.

Preferably, said characteristic comprises the chemical composition of the substance.

Additionally or alternatively, said characteristic may comprise the amount of a particular chemical in the substance.

Additionally or alternatively, said characteristic may comprise the purity of the substance.

BRIEF DESCRIPTION OF THE DRAWINGS

FIG. 30 is a flowchart showing the process followed for implementing stochastic resonance.

BEST MODE(S) FOR CARRYING OUT THE INVENTION

The best modes for carrying out the invention each involve systems and processes for analysing a pharmaceutical composition using NQR.

Figure 1:
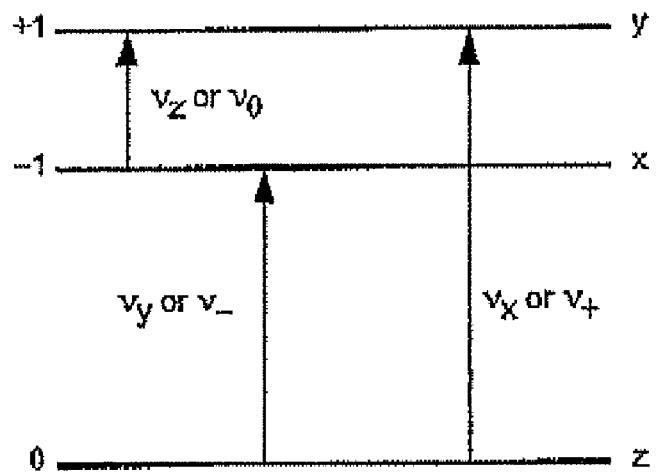
FIG. 1 is an energy level diagram showing the allowed transitions for a spin-1 nucleus such as $^{14}N$.

There are many chemical compositions that incorporate quadrupolar nuclei. One of the most important of these is $^{14}$N, a spin-1 nucleus, although there are many other quadrupolar nuclei that are commonly found in medicines, such as $^{23}$Na, $^{35}$Cl and $^{79}$Br. The energy level diagram and allowed transitions for a spin-1 nucleus such as $^{14}$N are shown in FIG. 1.

In the general case, there are three allowed transitions for $^{14}$N nuclei, two of these at discrete frequency, and the other at a frequency ($v_x$ or $v_+$) being the sum of the first two frequencies ($v_y$ or $v_-$, $v_z$ or $v_0$). The vast majority of these frequencies lie between 0.2 and 6 MHz.

These frequencies are related to quantities known as the nuclear quadrupole coupling constant NQCC and the asymmetry parameter η by equations (1), where:
 ($e^2qQ/h$) is the NQCC,
 e is the charge on the electron,
 h Planck's constant,
 $q=q_{zz}$ the maximum principal component of the EFG tensor and
 Q the nuclear electric quadrupole moment.

η, the asymmetry parameter, is defined as the difference between the other two components ($q_{xx}$ and $q_{yy}$) of the EFG tensor divided by q; it is a positive number lying between zero and one.

$$v_x = 3/4 \frac{(e^2qQ)}{h}(1+\eta/3) \quad (1)$$

$$v_y = 3/4 \frac{(e^2qQ)}{h}(1-\eta/3)$$

$$v_z = 1/2 \frac{(e^2qQ)}{h}\eta$$

Figure 2:
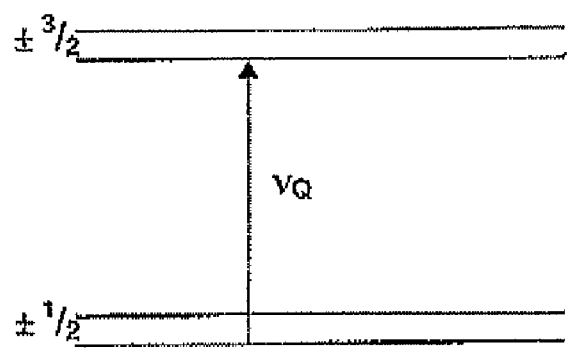
FIG. 2 is an energy level diagram showing the allowed transitions for a spin-$\frac{3}{2}$ nucleus such as $^{36}Cl$.

Spin-³⁄₂ nuclei such as $^{23}$Na, $^{35}$Cl and $^{79}$Br have two doubly degenerate levels as shown in FIG. 2, where transitions between these levels give rise to just one frequency equal to:

$$v_Q = 1/2 \frac{(e^2qQ)}{h}\left(1 + \frac{\eta^2}{3}\right)^{1/2} \quad (2)$$

Energy transitions at these frequencies induce NQR signals that can be generated by means of pulsed RF techniques, in which the $^{14}$N nuclei are subject to bursts of RF radiation at, or near to, their NQR frequency and the resulting transient signals monitored in the quiescent periods between pulses to detect generated NQR signals. The NQR signals are generated by the interaction of the nuclear magnetic moment with the magnetic component $B_1$ of the applied RF field, and can be of two types: free induction decays (FID) and echoes.

A FID is the decaying signal observed immediately following a pulse, while an echo is a regenerated signal with maximum intensity between RF pulses in a multiple pulse train.

The best mode of the present invention employs a system that uses pulsed RF techniques to irradiate a pharmaceutical substance, generate NQR signals therefrom and detect them, all during the production of the pharmaceutical substance. Furthermore, and importantly, the best mode uses a variety of different techniques to analyse the detected NQR signals in a manner so as to obtain a measure of one or more characteristics of the pharmaceutical substance and process this measure having regard to the requisite characteristic(s) of the pharmaceutical substance at the particular stage of production that the characteristics are measured. In this manner, the system provides a measure of the quality of the product, whereby suitable remedial action may be undertaken in the event that a measured characteristic deviates more than an allowable amount from the requisite characteristic to control the quality of the production of the pharmaceutical in real time.

According to the best mode, the RF radiation is generated in a number of ways: in one modes a planar single turn or spiral of copper wire or ribbon, which can also function as a receiver of the signals from an irradiated sample, is used to detect signals from tablets in blister packs; and in another mode, a conventional solenoid or bird-cage coil is used to detect signals from samples dispensed in containers. In a further mode, separate transmit and receive antennae are used.

Importantly, in each of these modes, the measures can be obtained in a non-invasive manner. For instance, if the measures are obtained in relation to pharmaceutical samples in the form of tablets that have already been packaged, the tablets need not be removed from their container in order for the measure to take place.

$^{14}$N signals are usually very weak and many responses must be accumulated to achieve an acceptable signal-to-noise ratio (SNR). For this purpose, the best modes use extended trains of pulses accumulating the observed responses between pulses to enhance the SNR.

One of these modes uses an extended train of pulses known as pulsed spin locking (PSL), which is represented by:

$$\alpha_0° - (\Sigma - \alpha_{90°} - \tau -)_n$$

where:
- α represents the pulse width, selected to optimize the signal,
- the subscripts denote the RF phase,
- τ determines the pulse spacing, which is 2τ after the first two pulses, and
- η determines the number of pulses in the train, whose optimum value depends on the relaxation times of the material.

The entire pulse sequence is repeated several hundred times for further signal averaging depending on the quantity of material in the sample and in the case of remote detection, its distance from the antenna.

Spurious signals, such as observed from piezoelectric materials, need to be eliminated. This is achieved by cycling the phases of the RF pulses and signals before processing, which in one mode is performed in the time domain, and in another mode is performed in the frequency domain, after Fourier transformation.

Phase-cycled multi-pulse sequences can be applied at ambient temperatures to many nitrogen-containing compounds of pharmaceutical interest to produce $^{14}$N line widths of several kHz or less. At this degree of resolution, distinction between the polymorphic forms of the chemical substance being analysed can easily be made, which is highly desirable for quality control purposes. Furthermore, the presence of two or more polymorphs in a mixture can be readily confirmed and their relative proportions determined with an accuracy that depends, inter alia, on the material, the concentration of each of the polymorphs and the pulse sequences used. This is of particular utility in circumstances where the manufacturer is obliged to specify the particular polymorph that is present in a drug, and/or the relative proportions of other polymorphs that may be present.

Since the pulse sequence repetition time is limited by the need to wait for the nuclear spins to recover their equilibrium magnetisation and this time is determined by the spin-lattice relaxation time $T_1$, $T_1$ is an important parameter that is measured before any analytical measurements are undertaken.

In pharmaceutical analysis, the important quantities determined by experiment are the quadrupole coupling constants (NQCC) and asymmetry parameters η, which function in much the same way as the chemical shift or rather the chemical shift anisotropy in NMR, since they also contain information on the asymmetry through the two other components of the EFG tensor, $q_{xx}$ and $q_{yy}$.

Because Laplace's equations holds, $$q_{xx} + q_{yy} = q_{zz} = 0 \quad (3)$$

there are only two independent parameters which define this tensor; unfortunately the direction cosines of these tensor components are not usually derived in measurements on powders—a single crystal is needed.

In one of the best modes, a knowledge of the two parameters, NQCC and η, as derived in an analysis algorithm is used in a processing algorithm to identify a material or a related compound, using a reference lookup table of NQR frequencies, stored within a database, which are obtained from published lists of materials.

As an example, consider performing an analysis using NQR of the antihypertensive drug Atenolol, which has the structure (1) with two different kinds of nitrogen atom, one amine, the other amide.

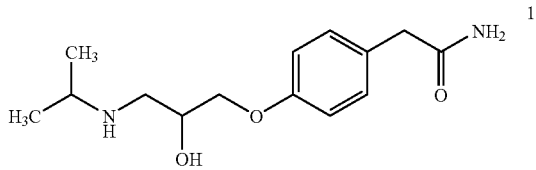

1

At room temperature, the NQR frequencies, NQCC and η are determined as:

I 0.47, 2.98, 3.50 MHz: NQCC=4.32 MHz, η=0.241

II 0.65, 1.60, 2.14 MHz: NQCC=2.493 MHz, η=0.433 in which the frequencies are combined according to equation (1) so that the largest is close to the sum of the other two. A comparison of these with the listed parameters in the lookup table for $Me_2NH$ at 77 K (4.65 MHz, 0.169) and acetamide (2.526 MHz, 0.375) leads us to assign I to the amine group and II to the amide.

These comparisons are rarely exact, or even nearly so, firstly because NQR frequencies in solids are averages over all molecular and torsional modes within the molecules and so are temperature dependent, and secondly, there are solid-state effects, just as in solid-state NMR, which can be rather large in the presence of hydrogen bonding to the atom containing the quadrupolar nucleus.

An important difference from NMR, however, is the much greater spectral range that is obtained in NQR. There are large differences in the frequencies of nuclei in different chemical functional groups, and even within the same functional group. While this may be a disadvantage in the design of the apparatus and location of the signal, it has one important consequence in pharmaceutical analysis in that NQR is a highly selective technique. It is a relatively easy matter to distinguish between different chemical species and different polymorphs; even if by coincidence the frequencies are the same, this is only likely to be true at a single temperature and in any case the relaxation times are almost certain to be different.

In another mode, theoretical calculations by Gaussian at the HF/6–31+G* level, are used in the processing algorithm to provide the reference values against which the calculated values of quadrupole coupling constants and η as derived in the analysis algorithm from the NQR scanning of the substances in-line, are checked, in cases where an accurate structure for the molecule of the chemical substance being analysed is available. Strictly speaking, such theoretical calculations predict the NQCC for a rigid molecule in the gas phase, but some allowance is made for solid-state effects and hydrogen bonding by including a cluster of molecules at the configuration they adopt in the solid state.

Examples of substances that may be analysed in this way include Gaussian calculations of the narcotics heroin and cocaine and heroin hydrochloride monohydrate for which X-ray crystal structures are available; in the case of the latter, two hydrogen-bonded molecules are used in the calculation, a total of 110 atoms, and NQCC and asymmetry parameters are predicted to within 15% of real time experimental values, as shown in Table 1 for the two protonated nitrogen atoms, N(1) and N(2) in the two different protonated heroin cations in the unit cell. It should be noted that the calculation gives the sign of the NQCC as well as their direction cosines with respect to the axial system used, whereas this information is not usually derivable from NQR experiments.

TABLE 1

Comparison of theoretical and experimental values of the $^{14}N$ quadrupole parameters in heroin hydrochloride monohydrate. *at 4.2 K

| Atom | Theory | | Experiment* | |
| --- | --- | --- | --- | --- |
| | QCC (MHz) | η | QCC (MHz) | η |
| N(1) | −1.575 | 0.098 | 1.328 | 0.108 |
| N(2) | −1.399 | 0.142 | 1.329 | 0.128 |

An important aspect of pharmaceutical development is the identification and selection of the appropriate polymorphic form, as this can have significant effects on the stability, processability and bioavailability of a pharmaceutical formulation.

As an important example, Furosemide (2) has at least two polymorphs, for both of which X-ray crystal structures have been published, enabling comparisons to be made with the expected point symmetry of the molecules in the solid state and providing an additional check on the polymorphic form.

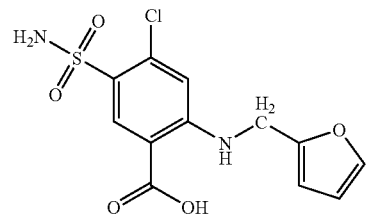

2

Figure 3A:
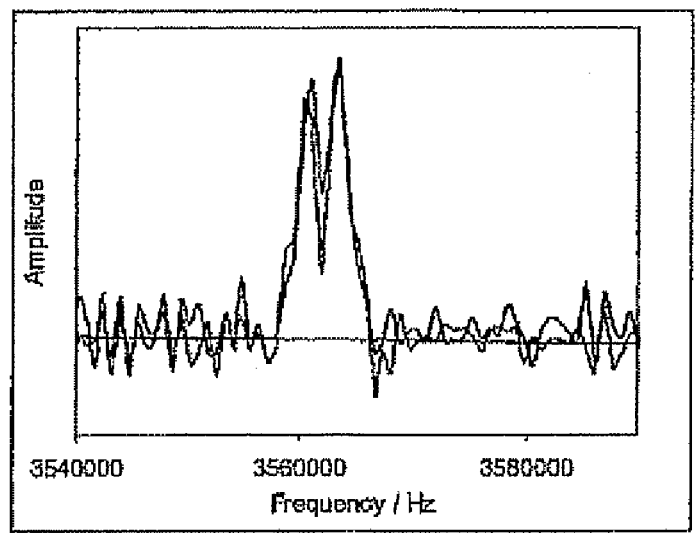
FIG. 3a is graph showing the amplitude of NQR signals plotted against frequency, detected from scans of phase I furosemide with a doublet peak at frequencies 3.564 and 3.561 MHz, splitting at approximately 2.35 kHz and line width of approximately 1.6 kHz for both lines.

The crystal contains two quadrupolar nuclei, $^{14}N$ and $^{35}Cl$, and NQR signals from both nuclei can been detected. In FIG. 3a, an example of the NQR signals detected from NQR scannings of two discrete samples of the polycrystalline polymorphic form of furosemide made by two different manufacturers, shows that both samples give rise to very similar $^{14}N$ NQR spectra; near 3.56 MHz a clear doublet is seen, assigned to the sulfonamide nitrogen, with peaks at 3.564 and 3.561 MHz at room temperature, and has line widths close to 1.6 kHz. The doublet structure is predicted from the crystal structure analysis of the polymorphic form I.

Figure 3B:
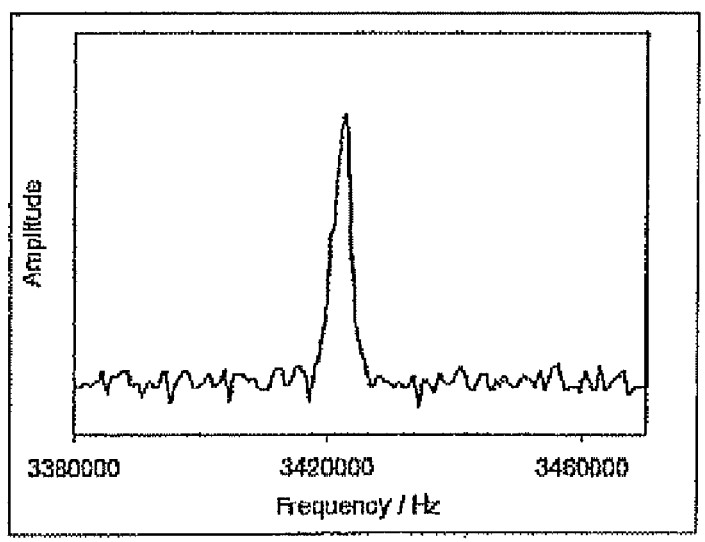
FIG. 3b is a graph showing the amplitude of an NQR signal plotted against frequency, detected from a scan of phase II furosemide with a singlet $^{14}N$ singlet signal at 3.422 MHz at room temperature with line width approximately 3 kHz.

In comparison with this, recrystallisation of this sample from n-butanol gives the metastable polymorphic form II, where the line frequency shifts to 3.422 MHz, as shown in FIG. 3b. The change of 0.141 MHz is easily observed when line widths are only a few kHz or less. In addition, the line is now a singlet in agreement with the prediction of the point symmetry of the molecule in this form.

For furosemide $^{35}Cl$, NQR signals have been detected at 77 K; where only one frequency is reported at 36.759 MHz. On NQR scanning the different samples of the polycrystalline polymorphic form of furosemide, NQR signals were detected at room temperature at the line frequency of 36.266 MHz, which provides an indication of the temperature effects for this nucleus. Notably, this line has a very short spin-lattice relaxation of 2 ms at room temperature, a value not untypical of the higher frequencies observed for $^{35}Cl$ nuclei in organic compounds. As a consequence, strong signals can be obtained in a few seconds.

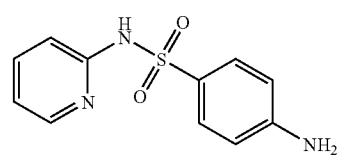

3

Another rather different example is the antibacteriocide sulfapyridine (3), which also exists in different morphological forms. In this case, the NQR spectra of material of a commercially manufactured raw sample is compared with material prepared by recrystallisation from solvents such as ethanol and acetone (Table 2).

Figure 4:
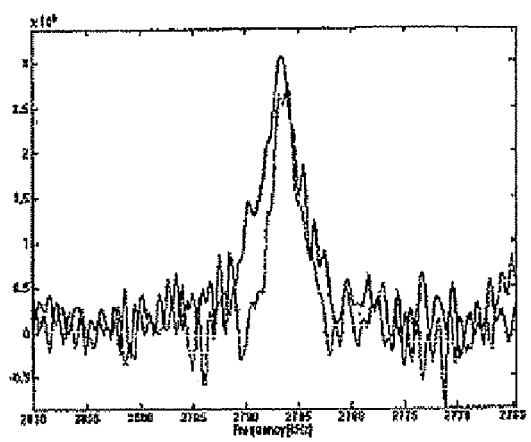
FIG. 4 is a graph showing a comparison of the amplitude of NQR signals plotted against frequency, detected from: a scan of the raw powder sample of sulfapyridine at room temperature, which is shown as a solid line: —; and a scan of the recrystallised sample of sulfapyridine from ethanol at room temperature, which is shown as a dashed line: - - - -, for line widths at the 2.787 MHz line.

Considering the 2.807 MHz line at 77 K, which has been tentatively assigned as $v_+$ of the —$NH_2$ group; at room temperature its frequency falls to 2.787 MHz and signals at this frequency can be seen in both the raw sample and the recrystallised sample indicating that they both consist of the same morphological form. However, their line widths are different as shown in FIG. 4, that of the recrystallised sample (2.5 kHz) being significantly less than that of the raw sample (4.0 kHz). The reason seems to be that, in general, NQR lines are inhomogeneously broadened, due partly to defects and crystalline imperfections but also to the presence of impurities or even strain in the material, factors alleviated by recrystallisation. This line broadening is used in one of the best modes in the analysing and processing algorithms to provide for quality control of the production of a pharmaceutical form of sulfapyridine.

Figure 5:
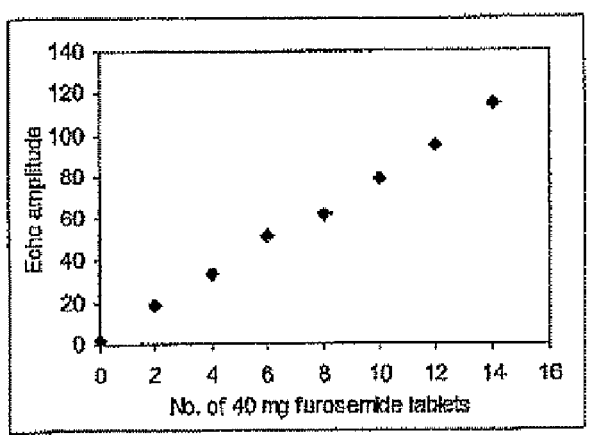
FIG. 5 shows two graphs, one plotting the echo amplitude of the $^{35}$Cl NQR signal intensity against the number of tablets detected from a scan of 40 mg furosemide tablets in a container; and the other plotting the integrated intensity of the $^{35}$Cl NQR signal intensity against the number of tablets detected from a scan of the same type of tablets.
Figure 5:
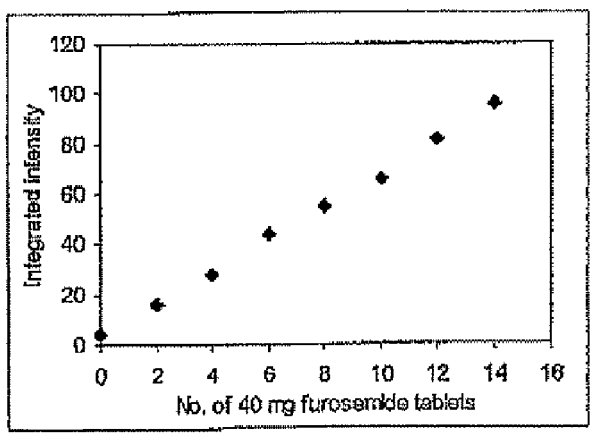

There is a reasonably linear dependence of peak signal intensity on sample weight. Tablets in a dispensing container are best examined in an RF probe with as homogeneous an RF field as possible across the sample, for example by the use of a coil of variable pitch. An example of the correlation between peak signal intensity and the number of tablets in a container is shown in FIG. 5, where in a preliminary experiment, a series of eight NQR scans were performed in which the number of tablets was increased by two between each scan; and the results recorded as shown in Table 3. FIG. 5 plots the mean integrated echo intensities against the number of tablets.

Following these experiments, one sample consisting of 4 tablets was chosen as an unknown; from the integrated echo intensity, the mean number of tablets was estimated to be 3.82±0.30, with confidence limits of 95%.

These results would be improved by adopting one or the other of the best modes involving better coil design and thermostatting of the samples and RF probe in contrast to the equipment used to perform the experiments.

TABLE 2

$^{14}N$ NQR Parameters of Sulfapyridine (Sigma) at approximately 25 C.

| Raw Powder | | | From Ethanol | | From Acetone | | |
|---|---|---|---|---|---|---|---|
| v/MHz | $\Delta v_{1/2}$/kHz | $T_1$/s | v/MHz | $\Delta v_{1/2}$/kHz | v/MHz | $\Delta v_{1/2}$/kHz | $T_1$/s |
|  |  |  | 1.480 ± 0.001 | 1.8 ± 0.2 |  |  |  |
| 2.284 ± 0.001 | 5.0 ± 0.5 | 1.0 ± 0.1 | 2.283 ± 0.001 | 3.0 ± 0.2 |  |  |  |
| 2.393 ± 0.001 | 3.5 ± 0.5 | 1.4 ± 0.1 | 2.392 ± 0.001 | 1.8 ± 0.2 |  |  |  |
| 2.787 ± 0.001 | 4.0 ± 0.4 | 0.65 ± 0.5 | 2.786 ± 0.001 | 2.5 ± 0.3 | 2.895 ± 0.001 | 2.8 ± 0.3 |  |
| 2.924 ± 0.001 | 3.8 ± 0.4 | 0.70 ± 0.5 | 2.923 ± 0.001 | 2.5 ± 0.3 | 3.060 ± 0.001 | 1.0 ± 0.1 | 0.01 ± 0.001 |

Table 2 lists some of the NQR parameters at 25 C of the three different samples of the examined drug; it is clear that the sample as supplied has the same frequencies and spin-lattice relaxation times as that recrystallised from ethanol, as expected, but different line widths, as indicated. It is also clear that recrystallisation from acetone has produced a different form, which subsequent analysis has shown to be an acetone solvate. Both frequencies and relaxation times are different, illustrating the solid state effects.

The effect on the line width and line shape are most marked when the sample under analysis actually contains both crystalline and amorphous forms of the same substance, a circumstance sometimes encountered in the manufacture of drugs. The crystalline form gives rise to normal pulsed $^{14}N$ NQR spectra, with line widths typically not more than a few kHz, and often less. The amorphous phase, however, can have much larger line widths, often 20 kHz or more, a definite line shape, possibly with structure, and will not in general be readily observed under the same conditions which favour the detection of signals from the crystalline regions.

In one mode, broad lines are detected by adjustments to the probe and pulse sequence used and a faithful reproduction of the line shape is obtained by a modification of the technique of Fourier transform spin-echo mapping spectroscopy (FT-SEM). The sharp distinction between the two techniques enables the amorphous and crystalline phases to be separately detected with a sensitivity that depends on their relative proportions, which is also derived from the measurements.

TABLE 3

Measurements obtained for quantitative analysis of furosemide tablets using $^{35}Cl$ NQR.

| No. of 40 mg tablets | Mean echo amplitude | Mean integrated intensity | Mean SNR |
|---|---|---|---|
| 0 | 1.9 | 3.6 | 1.7 |
| 2 | 18.9 | 15.6 | 4.3 |
| 4 | 33.9 | 27.8 | 8.5 |
| 6 | 51.2 | 43.4 | 12.2 |
| 8 | 62.3 | 54.3 | 10.8 |
| 10 | 78.9 | 65.4 | 14.7 |
| 12 | 95.1 | 81.6 | 19.6 |
| 14 | 115.0 | 95.5 | 24.0 |

A serious disadvantage of NQR methods involving $^{14}N$ has always been the relative weakness of signals detected at such low frequencies, in comparison with many hundreds of MHz common in modern NMR spectrometers.

According to one of the best modes, this problem is considerably reduced by the use of cryogenic RF coils, which improves the SNR, particularly at the low NQR frequencies characteristic of $^{14}N$ at which sample losses are minimal. This mode also involves the use of polarization-enhanced NQR (PE-NQR). In this method a sample containing both $^1H$ and quadrupolar nuclei, is polarized for sufficient time in a high field, say at a frequency $v_H$ of 40 MHz; the field is then switched off or the sample ejected. As its value falls, level crossing occurs between the $^1H$ levels and the quadrupolar levels (provided the latter lie at less than 40 MHz) whereupon the latter rapidly reach the same spin temperature as the former. A pulsed NQR scan in zero field is then performed to give a signal whose intensity is enhanced by a factor close to the ratio of the two frequencies $v_H/v_Q$.

Several specific embodiments will now be described, which are directed towards various systems and methods for implementing the best modes using NQR for performing chemical analysis of either of the two well known medicines, furosemide (2) and sulfapyridine (3), during production runs of different pharmaceutical forms of these medicines. The same reference numerals are used to describe and depict corresponding elements of the various systems and methods as they are referred to between the embodiments.

The first of these embodiments is directed towards a quality control system and process for providing quality control using NQR analysis of mass-produced furosemide tablets packaged in a blister pack.

Figure 6:
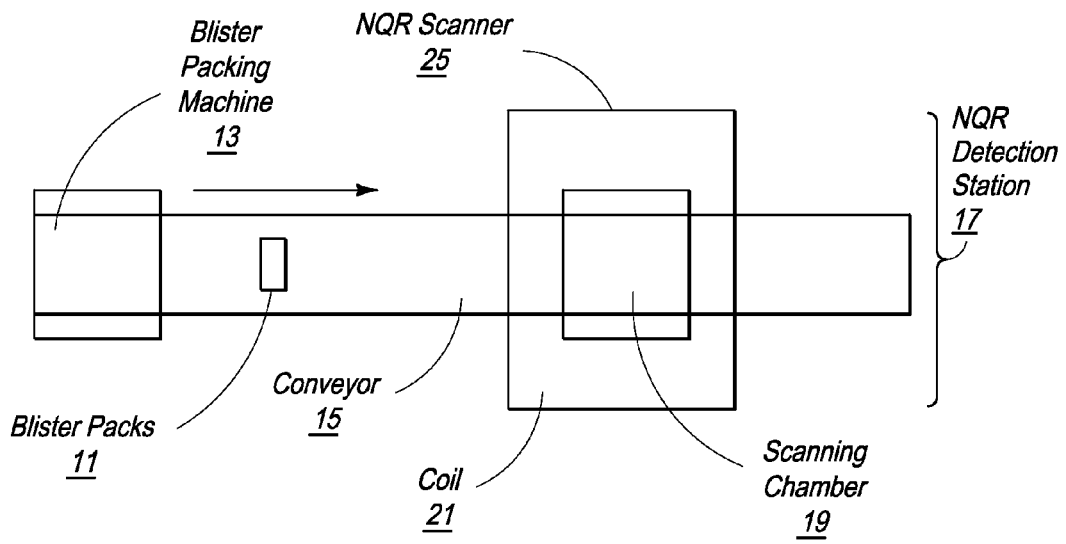
FIG. 6 is a block diagram showing the location of the NQR detection station within the production line of blister packaged furosemide tablets in accordance with the first embodiment.

As shown in FIG. 6, blister packs 11 are dispensed from a blister-packaging machine 13 along a conveyor 15.

Figure 7:
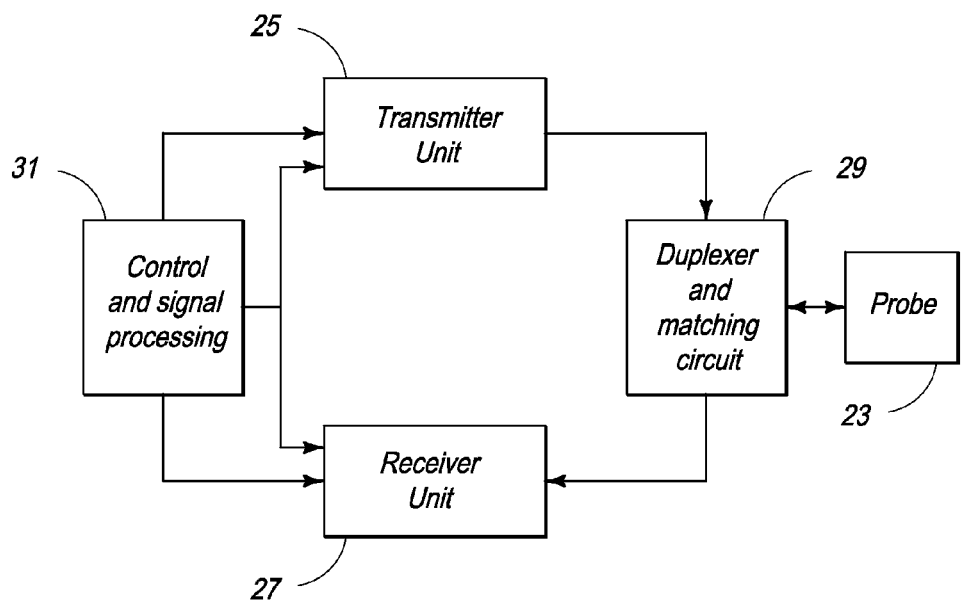
FIG. 7 is a block diagram showing the NQR scanner in accordance with the first embodiment.

The conveyor 15 transfers the blister packs 11 in horizontal repose, sequentially to an NQR detection station 17 comprising an analysing volume in the form of a small cubic scanning chamber 19 circumscribed by a single-turn flat resonant coil 21. The scanning chamber 19 is shaped to closely accommodate a blister pack 11, and the coil is configured to provide an extremely homogeneous magnetic field throughout the chamber 19, when irradiating the same with electromagnetic energy. The coil 21 and scanning chamber 19 are housed within a shield 22 to isolate the coil and chamber from external electromagnetic interference. The coil 21 forms part of a probe 23, which in turn forms part of an NQR scanner 25 shown in FIG. 7.

The arrangement of the coil relative to the scanning chamber is such that magnetic field lines produced by the coil are orientated to be mostly parallel to the metal surfaces of the blister pack, such as the aluminium foil seal along the bottom of the blister pack, to prevent field inhomogeneities within the volume circumscribed by the coil. If the field was to impinge upon a metal surface orthogonally, then eddy currents would be induced in the metal surface which oppose the applied field and thus destroy this field and the sensitivity of the coil in this area. By making the field lines parallel with the metal surface of the pack, the field lines do not interact and the field strength is unaffected allowing samples to be detected with equal strength, regardless of how close they lie to the metal surface.

The hardware componentry of the NQR scanner 25 is of known design and will not be described in detail, suffice to say that it comprises the principal functional components of: pulse generating and transmitting means; signal receiving and processing means; and NQR signal analysing means.

These functional components in the present embodiment are implemented by discrete hardware components comprising: a control and signal processing unit 27, a transmitter unit 29, a receiver unit 31, and a duplexer and matching circuit 33, which in turn interfaces with the probe 23.

The control and signal processing unit 27 forms part of a computer for generating the pulse signal sequence to be transmitted by the transmitter unit 29 to the probe 23, via the duplexer and matching circuit 33, and thus in combination with the transmitter unit constitutes the pulse generating and transmitting means. The control and signal processing unit 27 also controls the operation of the transmitter unit 29 and the receiver unit 31 so that alternate transmitting, receiving and signal processing may take place using the one coil, and thus in combination with the receiver unit 31 constitutes the signal receiving and processing means. Finally, the computer of the control and signal processing unit 27 operates a computer program specifically designed to perform chemical analysis of a blister pack 11 disposed within the scanning chamber 19, following scanning thereof, to determine whether the tablets within the blister pack meet the prescribed quality control standards for the mass produced pharmaceutical form of furosemide. Thus, the computer and analysis software thereof constitutes the NQR signal analysing means of the invention.

Figure 8:
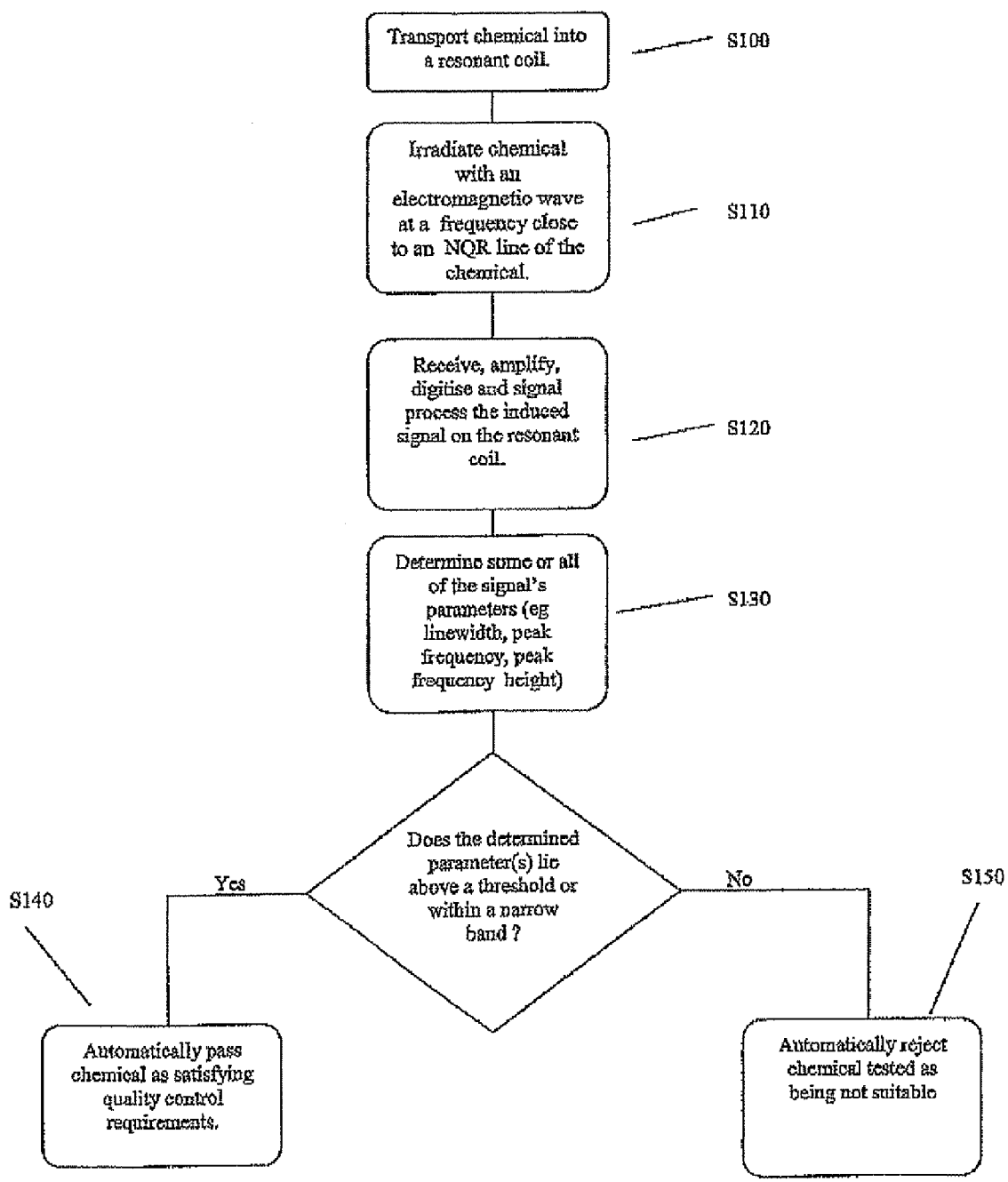
FIG. 8 is a flowchart demonstrating the general functional processes performed by the quality control system of the first embodiment.

As shown in FIG. 8 of the drawings, the process followed by the quality control system in the present embodiment firstly involves the blister pack 11 being dispensed from the blister-packaging machine 13, and transporting it s100 to the NQR scanning station 17 and into the scanning chamber 19. The NQR scanner 25 is then operated to perform either one or a series of quality control tests on the blister pack, depending upon the quality control checks prescribed for the particular production process being undertaken. For example, it may be prescribed to only check for the correct number of tablets inserted into the blister pack, i.e. that a tablet is included at each blister of the pack and that none have been missed. Alternatively, or additionally, the particular identity of the chemicals present in each pack may be checked and/or the purity of such chemical checked to accord with certain prescribed quality control parameters for such.

In each of these tests, the probe 23 irradiates s110 the blister pack 11 with electromagnetic RF radiation at a frequency close to the prescribed NQR line of the quadrupolar nuclei in the composition, via the coil 21. In the present embodiment this will be at 3.56 MHz for the sulphonamide nitrogen of the polymorphic form I of polycrystalline furosemide and 36.266 MHz for the $^{35}Cl$ nuclei. The resultant induced signal on the coil 21 is then received, amplified, digitised and signal processed s120 by the receiving and processing means to isolate the NQR signal therefrom for each test. The analysis program is then invoked to determine prescribed parameters s130 of the isolated NQR signal, which includes its line width, peak frequency and peak frequency height, dependent upon the particular test being performed. The measured parameters are then compared s135 against prescribed references that may require the measured parameters to lie above a threshold or within a narrow band to conform to an acceptable standard of quality. If the measured parameters in each test conform to the standard of quality s140, then the blister pack 11 automatically continues on its way through the NQR scanning station 17 and along the conveyor 15, satisfying the quality control requirement. If the measured parameters for any particular test do not reach the requisite threshold or fall within the prescribed range, then the blister pack is automatically rejected s145 and diverted from the conveyor line 15. The diversion further sub-diverts the rejected blister pack into separate collection zones, classified according to the particular test resulting in the rejection.

Importantly, the pulse generating and transmitting means generates a plurality of different pulse sequence schemes for the different tests performed and the receiving and processing means is controlled to receive signals produced therefrom according to the particular pulse sequence scheme adopted for the particular test being performed, at the appropriate times. The analysing means operates in parallel and concomitantly with the pulse generating and transmitting means and the receiving and processing means, using the NQR signal isolated by the receiving and processing means as input data for the particular test being analysed.

Figure 9:
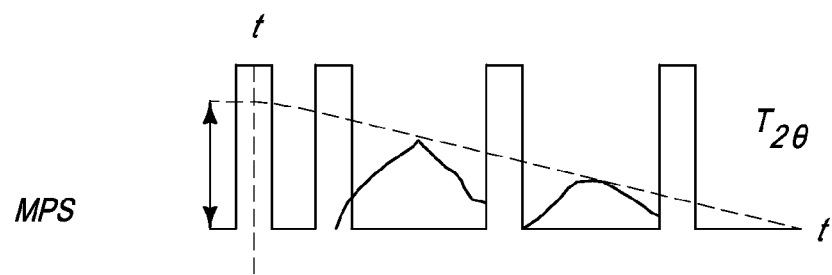
FIG. 9 is a signal diagram showing an amplitude-time graph of a multiple pulse sequence as described in the first embodiment.

In the present embodiment, the first quality control test involves checking the amount of targeted pharmaceutical present, which as previously described is derived from the correlation of peak signal intensity to the weight of sulphonamide nitrogen of the polymorphic form I of polycrystalline furosemide and of the $^{35}Cl$ nuclei, which in turn correlates to the number of tablets in the blister pack. To perform this test, the pulse generating and transmitting means generates a phase-cycled multi-pulse sequence signal of the PSL variety as shown in FIG. 9 and transmits it via the duplexer and matching circuit 29 to the probe 23. A phase-cycled multi-pulse sequence is used to enhance sensitivity (SNR) and resolution in preference to other known techniques for enhancing sensitivity and resolution such as double resonance or cooling of the chemical substance being scanned, both of which have serious disadvantages making them inapplicable for use with real time, in-line chemical analysis.

As shown in dashed outline, the receiving and processing means isolates an NQR signal that is an echo, which decays with a time constant $T_{2e}$. The analysing means is then invoked to extrapolate back the peak intensity of the echo signals, to the centre of the first pulse ("zero time") to give an intensity I, which is taken to be a measure of the quantity of the material. The analysing means performs a table lookup of the intensity to verify whether it corresponds to the number of tablets prescribed for each blister pack. If so, then the test is successful and the process moves to the second test. If not, then the blister pack is rejected and the conveyor engaged to move the blister pack out from the scanning chamber 19 for subsequent diversion to a reject zone.

The second test that is performed provides quality control with respect to the purity of the crystal structure of the furosemide tablets. In order to do this, use is made of the FID time $T_2^*$ and the spin-spin relaxation time $T_2$. As previously described, nearly all NQR lines seem to be inhomogeneously broadened due to imperfections or impurities in the crystal, which arise from methods by which the chemical substance being analysed has been prepared, crystallised and mechanically handled. Consequently, a pulse is transmitted to generate an NQR signal with a FID whose time constant depends on $T_2^*$ to obtain a measure of the total frequency distribution function, which is the mathematical convolution of the inhomogeneous (or static) frequency distribution contributed by imperfections or impurities in the crystal structure constituting the chemical makeup of the furosemide tablets, and the homogeneous frequency distribution contributed by the crystal structure itself. Then a pulse sequence is transmitted to generate a decaying signal whose time constant depends on $T_2$ to obtain a measure of the homogeneous frequency distribution of the crystal structure of the furosemide tablets.

Figure 10:
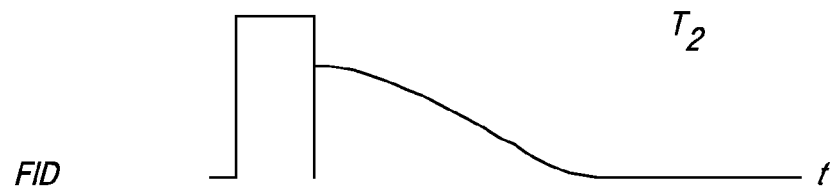
FIG. 10 is a signal diagram showing an amplitude-time graph of a free induction decay signal as described in the first embodiment.

In the present embodiment, the total frequency distribution is derived from the pulse generating and transmitting means irradiating the blister pack with a simple effective pulse of 90° in width. As shown in FIG. 10, the decaying signal that follows it is governed by $T_2^*$. This signal is received and processed by the receiving and processing means to isolate an NQR signal representative of the FID signal. The frequency distribution of the inhomogeneous broadening is then derived by using an extended time echo (ETE) pulse sequence to obtain a frequency distribution indicative of only the homogeneous components of the pharmaceutical composition.

Figure 11:
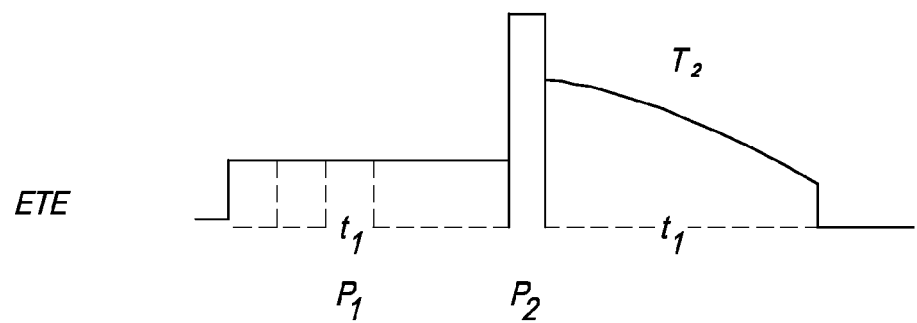
FIG. 11 is a signal diagram showing an amplitude-time graph of an extended time echo pulse sequence as described in the first embodiment.

The ETE pulse sequence is characterised by the pulse generating and transmitting means generating a long low-power RF preparation pulse $P_1$ of width $t\omega > T_2$ followed immediately by a short, non-selective refocusing pulse $P_2$ of width 180°, as shown in FIG. 11.

Such a pulse sequence stimulates an NQR signal to be emitted by each of the quadrupolar nuclei $^{14}N$ and $^{35}Cl$ at different frequencies, immediately following $P_2$. This NQR signal is received and isolated by the receiving and processing means as a decaying signal, which lasts for a period of time $t_1$ commensurate to that of $P_1$, but with a decay governed by $T_2$ rather than $T_2^*$, i.e. it is governed by a homogeneous frequency distribution. Since $T_2$ is much longer than $T_2^*$, the result is a signal of longer duration less affected by any deadtime following $P_2$. In short, a two-pulse echo decay arises from just one shot with an increase in signal intensity in the frequency domain.

The $90°_{\it eff}$ pulse and the ETE pulse sequence is transmitted and the resultant FID and echo pulses received by the signal receiving and processing means in a cycle that is repeated several hundred times, where the received signal is separately averaged to isolate the FID signal governed by $T_2^*$ and the echo signal governed by $T_2$ to provide a representative indication of the total and homogeneous distribution functions, respectively, as described above.

The analysing means is subsequently invoked to perform a mathematical deconvolution of the representative indications to separate out the contribution made by the inhomogeneous part of the frequency distribution from the total frequency distribution using the homogeneous frequency distribution. The inhomogeneous part is then quantified to provide a detected measure of the chemical imperfections or impurities of the furosemide tablets. This detected measure is then compared against a reference measure for quality control purposes. If the derived measure does not fall within a prescribed tolerance when compared with the reference measure, the blister pack is rejected as containing too many impurities and the conveyor operated to move the blister pack out from the scanning chamber 19 for subsequent diversion to a reject zone. If the derived measure does fall within the prescribed tolerance, the test is successful and the process moves to the third test.

The third quality control test that is performed is for detecting the presence of undesirable materials in a given pharmaceutical using a pulse sequence adapted to cover a wide frequency range.

Although not related to the present embodiment, in an embodiment of the invention adapted for performing quality control tests on the antimony containing substance Tarter Emetic, of potential use in the treatment of certain tropical diseases, the presence of other antimony-containing materials of much higher toxicity must be checked. Using NQR to detect the presence of $^{121}Sb$, is relatively straightforward. Similarly, this test is relevant to the analysis of diluents, impurities or decomposition products that may be present, due for example to unpredicted or unexpected circumstances in the process of manufacture.

Such undesirable materials are distinguished by identifying the particular atomic nucleus of the chemical present using nutation spectroscopy. By measuring the nutation frequency $\omega\pi$ of a quadrupolar nuclei, in a given RF field where the amplitude $B_1$ is known, the gyromagnetic ratio $\gamma Q$ of the quadrupolar nuclei can be derived, which in turn can unequivocally identify the nucleus. This arises from equation (4), wherein:

$$\omega\pi = \gamma Q B_1 f(\theta, \phi, \pi) \qquad (4)$$

Equation (4) must be averaged over all allowed values of $\theta$ and $\phi$. The precited two dimensional nutation line shapes are known for several nuclear spin quantum numbers and are used to deduce the gyromagnetic ratio $\gamma Q$ as well as the asymmetry parameter $\eta$. The nuclear spin quantum number is then deduced from the number of NQR transitions associated with a given impurity and the ratio of the frequencies using known methods.

Concurrent with performing each of the tests, the information or data gathered during the QR scanning process is automatically stored for future use. This information or data is securely stored in a database so that it may constitute scientific evidence for proving quality of the particular batch of the pharmaceutical at a later time, if necessary.

In the present implementation of this auto documentation system, and dependent upon what other tests or processes are performed by the scanning system as described in subsequent embodiments, the computer records the following information:

(i) Batch Number
(ii) Operator(s)
(iii) Company Name & Location
(iv) Time of Manufacture
(v) Target Pharmaceutical(s)
(vi) Undesired pharmaceutical(s) searched for (if any)
(vii) Peak heights (if recorded)
(viii) NQCC and asymmetry parameters (if calculated)
(ix) Line-widths measured (if any)
(x) Technique(s) used to determine parameters (pulse sequence, coil volume, analysing process)
(xi) Calibration information
(xii) Predetermined laboratory information used (eg NQR frequencies).
(xiii) Tagged substance search for (if any).

All of this information is formatted into a document, which can be printed and signed by an operator and a witness and later used as evidence, if such a requirement arises.

The information can also be used by the drug producer or distributor to determine if the pharmaceutical has aged. If later measurements determine that the signal strength is much lower than it was at the time of production, then the sample can be deemed to have aged.

Figure 24:
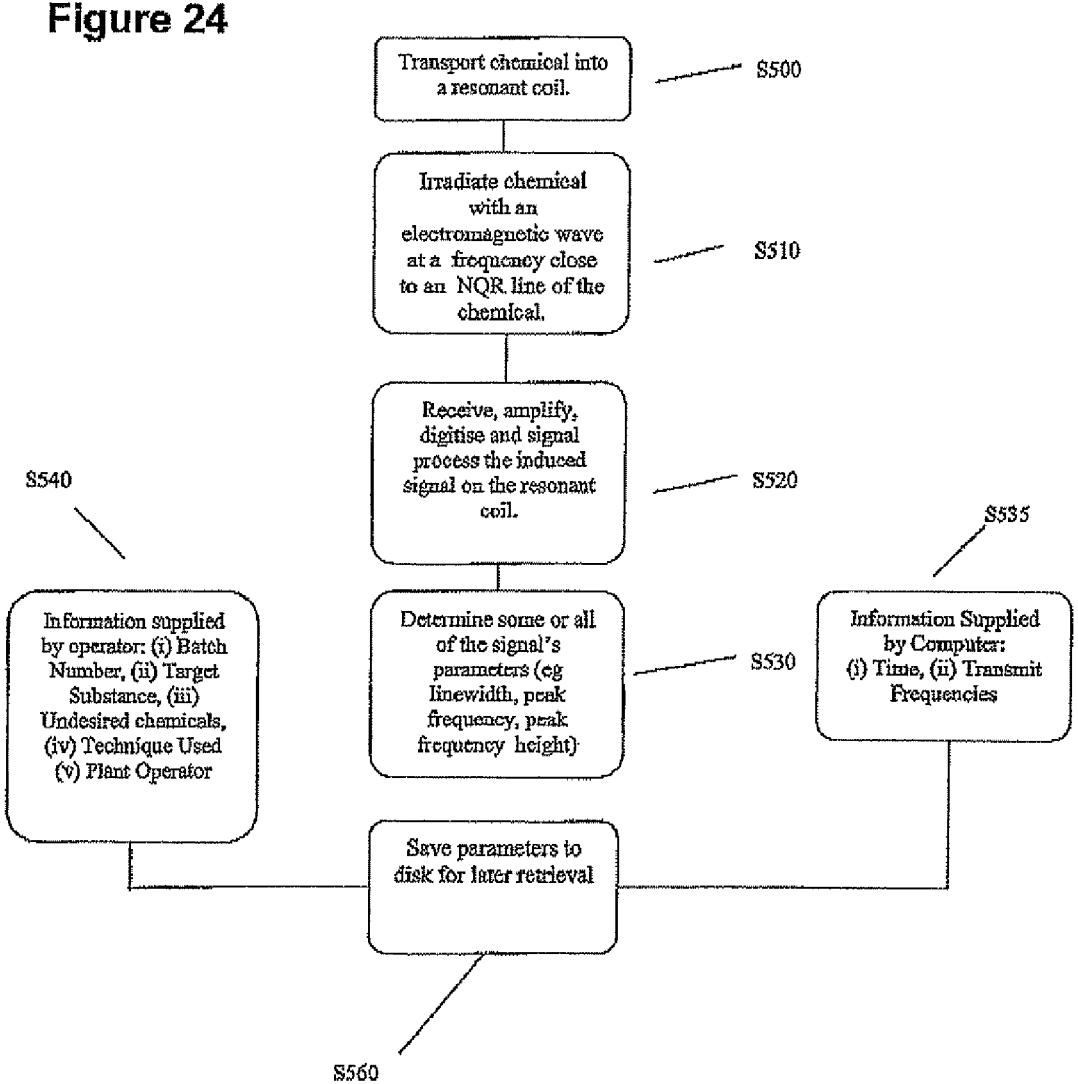
FIG. 24 is a flowchart showing the process followed for implementing auto-documentation in conjunction with the tests performed for quality control in accordance with the first embodiment.

As shown in FIG. 24, a sample is transported into a QR scanner S500 and irradiated with a pulse sequence S510. The signal that exists on the QR scanner's coil is amplified, digitised, filtered, apodised and Fast Fourier Transformed into frequency space S520. Here the characteristics of the signal, as stated in (i)-(xiii) S530, S535, S640 are stored on computer and printed out for filing S560.

The second embodiment is substantially the same as the first embodiment, except that it is directed towards a system and method for analysing furosemide tablets packaged in container form for quality control purposes and for adopting an alternative configuration for conveying the containers. Importantly, the second embodiment is directed towards an improved system and method for testing for the number of tablets dispensed into a container, whereby such dispensing can be more prone to variations occurring in the number of tablets dispensed, especially where containers containing relatively large numbers of tablets are produced and/or different dispensing runs are involved for dispensing different numbers of tablets for differently sized containers.

The present embodiment adopts four main steps for determining the number of tablets within a container:

(i) determining the environmental temperature;
(ii) calibrating the QR scanner;
(iii) measuring the QR signal of a container which contains an unknown numbers of tablets using a reproducible technique; and
(iv) determining whether the signals lies within the correct bounds for the number of tablets as to be specified on the label of the container.

The key issue with each of these steps is achieving a reproducible technique that can be applied to the container repetitively and achieve the same signal intensity. This is required because a widely varying signal intensity will result in incorrect numbers of tablets being determined, which limits the extent to which NQR can be used in quantitative quality control.

In previous techniques involving the use of NQR, such as those used for QR scanning of explosives in luggage, it was not critical that the signal was reproducible from one analysis to the next. For instance, the signal intensity from one particular explosive could vary by as much as 200%. Thus, the main task of a scanner in such applications was to simply to detect the explosive regardless of its signal intensity. If the signal intensity was allowed to vary the same extent with quality control measurement for determining the number of tablets in a container then, such a measurement would not be able to produce the correct number of tablets reliably and the technique would not be commercially viable.

Hence in the present embodiment, a number of features have been combined which allow for improved measurement reproducibility of the QR signal intensity. These features include:

(i) a temperature probe to determine the temperature of the surroundings and/or the sample of interest;
(ii) a coil which has an extremely homogeneous magnetic field;
(iii) a Q switching device;
(iv) a calibration step to accurately know the expected signal intensity; and
(v) the use of a multi-pulse echo train and backward projection.

The multi-pulse echo train also has characteristics to mitigate the temperature anomaly offset problem by not causing any fluctuations in signal intensity.

It is known that NQR frequencies drift with temperature. Some NQR frequencies are more susceptible to temperature variations than others. During pharmaceutical production, because of the large air space in the factory and the fact that it is difficult to thermally equilibrate this large volume, a pharmaceutical will be exposed to a variety of different temperatures during its production. Additionally, the pharmaceutical may still be warm after being dried and processed quickly. Consequently, it is necessary to measure the temperature of the pharmaceutical and/or the surroundings to more accurately determine the frequency of the transition line of the pharmaceutical. Hence, the present embodiment detects both the temperature of the surroundings and the temperature of the pharmaceutical by the use of probes.

Figure 12:
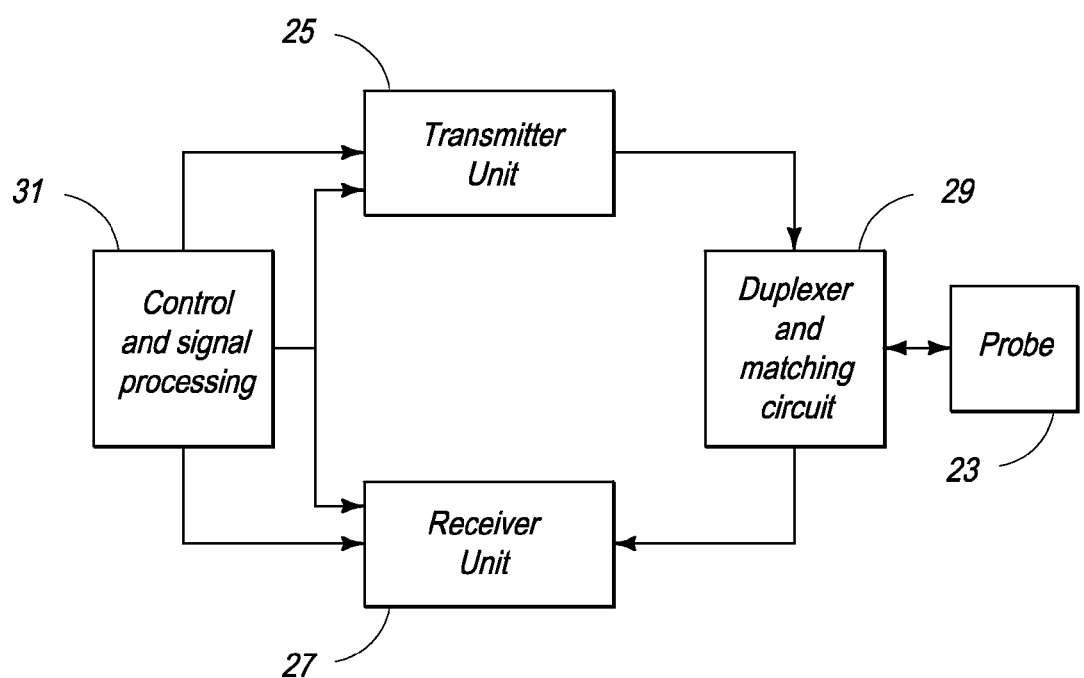
FIG. 12 is a block diagram showing the NQR scanner in accordance with the second embodiment.

As shown in FIG. 12 of the drawings, in order to determine the temperature of the surroundings, an external temperature probe 201, such as Monitor Sensors (Aust.) EA-TA1-01 is connected to the computer of the control and signal processing unit 27 to input a measure of the ambient temperature in the vicinity of the conveyor to the system. To determine the temperature of a sample, an IR gun such as a Digitech QM7222 Infra Red Thermometer, is modified to provide a tablet temperature probe 203 to input a temperature signal indicative of the tablet temperature into the computer of the control and signal processing unit 27. By measuring these temperatures, the frequency of the applied pulse sequence is more accurately determined. Accordingly, the control and signal processing unit 27 is designed to adjust the frequency by measuring the temperature and looking up a table or calculating what the quadrupole resonance frequency should be at that temperature, using the known temperature-frequency relationship for the NQR line of interest, and then adjusting the transmit frequency to this value. By making the frequency as close as possible to the correct frequency, the signal remains stable and does not vary in magnitude, thereby allowing reproducible measurements.

Generally NQR signal intensity increases as the temperature is lowered. As different tablets may be at different temperatures, it is necessary to correct for the effects of the increasing signal strength at lower temperatures by normalising the recorded signal strengths against their recorded temperature. To complete this step the temperature is recorded and a 'temperature multiplier' is calculated using the known signal intensity-temperature relationship. This signal intensity multiplier is used later during the process.

To limit the effect of temperature upon the measurement, it is preferable that the temperature of the factory is kept at a constant temperature via air conditioning and the sample is allowed to cool and thermally equilibrate with the surroundings before the measurement is begun. Both of these factors help to produce reproducible signal strength measurements and consequently result in an accurate measure of the number of tablets dispensed into a container.

In order to accurately and reproducibly determine the number of tablets contained in a container, a calibration of the quality control system is performed before undertaking any measurements in this regard.

Figure 13:
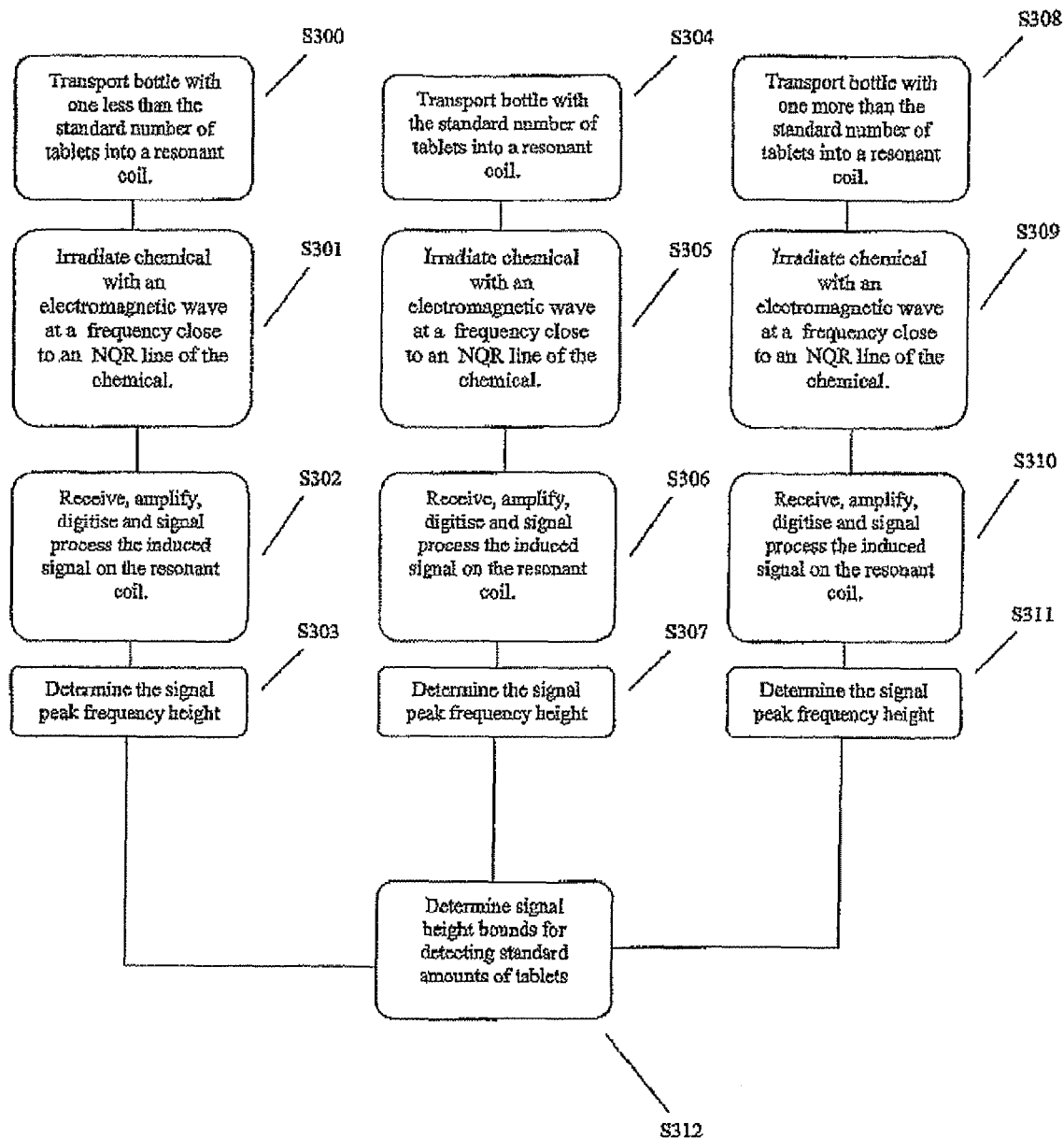
FIG. 13 is a flow chart showing the calibration sequence process as described in the second embodiment.

As shown in FIG. 13, three different containers are measured within the QR scanner. The first contains one less tablet than the required number of tablets in a container, the second contains exactly the required number of tablets in the container and the third contains one more than the required number of tablets in a container.

To perform the calibration process, the three containers are sequentially in time placed onto a conveyor belt and moved into a QR scanning coil S300, S304, S308. Once one of the containers is within the coil, the transmitter sends an amplified pulse sequence at a frequency close to the resonant frequency of the substance of interest to the coil; preferably this frequency is the frequency determined during the measurement of the temperature S301, S305, S309. The pulse sequence used in this particular application is a long multiple pulse echo train with phase cycling. The phase cycling is used to eliminate any piezoelectric or magneto-acoustic ringing which may be present in the sample being scanned. An example of a suitable phase cycling pulse sequence is:

$$90°-\tau-[180°-2\tau-270°-2\tau-0°-2\tau-90°-2\tau-]_n$$

where:
the phase indicates the phase of pulse;
$\tau$ is time interval in between pulses;
the section in brackets is repeated n times.

The amplified pulses generate an AC magnetic field which interacts with the quadrupolar nuclei tipping them momentarily out of alignment. After each pulse has been applied there is initially a period of dead time in which no measurement occurs followed by the acquisition period before the next pulse is applied. During the dead time period a Q switch is switched into the circuit to drain the transmit pulse energy out of the coil quickly such that the QR acquisition can begin sooner than normal. This allows an increase in signal to noise.

An example of a suitable Q switch is a triad, which is switched into the circuit at the end of the transmit pulse. The triac slowly switches itself off over time and once it has done, the acquisition stage can begin.

In steps S302, S306 & S310, the signal that exists on the coil is amplified, mixed down to form two out-of-phase quadrature signals and these are sampled by an analog-to-digital converter (ADC) to create digital representations of the same. These are then filtered, apodised, thresholded, multiplied by the temperature multiplier determined previously and fast Fourier transformed to produce a peak in frequency space S303, S307 and S311. It is this frequency peak that is used to determine the number of tablets within the container.

After each pulse the acquisition signal collected is Fourier transformed and the peak height and time are recorded. At the end of the pulse sequence the peak heights recorded during the measurement are curved fitted with respect to time and backward projection is used to determine the peak height that would have occurred at the centre point of the first pulse of the sequence. It is this value that is used to determine the calibration.

Figure 14:
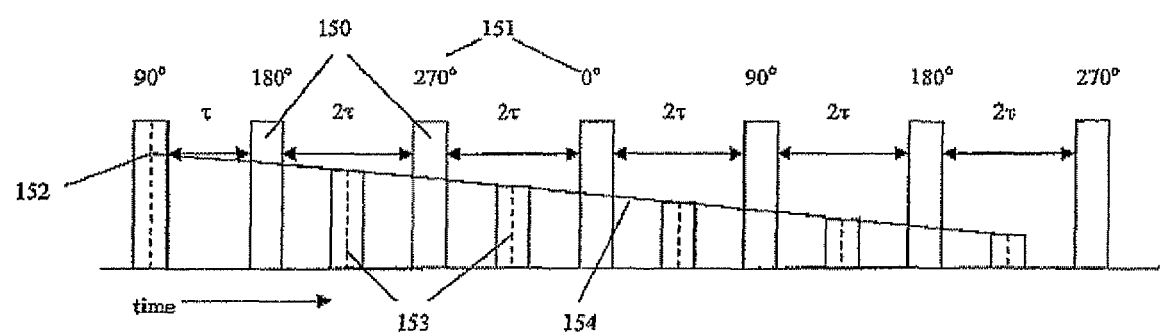
FIG. 14 is a signal diagram showing an amplitude-time graph of the phase cycling echo sequence as described in the second embodiment.

FIG. 14 shows the technique graphically. The pulses of the sequence 150, their respective phases 151 and time separation are shown forming the phase cycling echo sequence. The signal strength of each echo is shown by the blocks 153, which decay away over time. The heights of these blocks are backwardly projected 154 to reveal the height that would have occurred at the centre of the first pulse 152.

Typically, the peak heights determined in this manner will decay away in time as the pulses of the pulse sequence are repeatedly applied. It has been found that the heights of these peaks decays at different rates according to the particular circumstances during the measurement; however the peak height that would have occurred above the centre of the first pulse is more consistent. Therefore it is this value that is used to indicate the measured signal strength.

For each of the three containers this value at the centre of the first pulse (CFP) is used to form a linear fit through the three points and then determine bounds within which the signal from the CFP has to lie to identify the correct number of tablets. These bounds can be set as narrowly as 5% of the peak value or as much as 50% of the peak value depending upon the slope of the linear fit.

Figure 15:
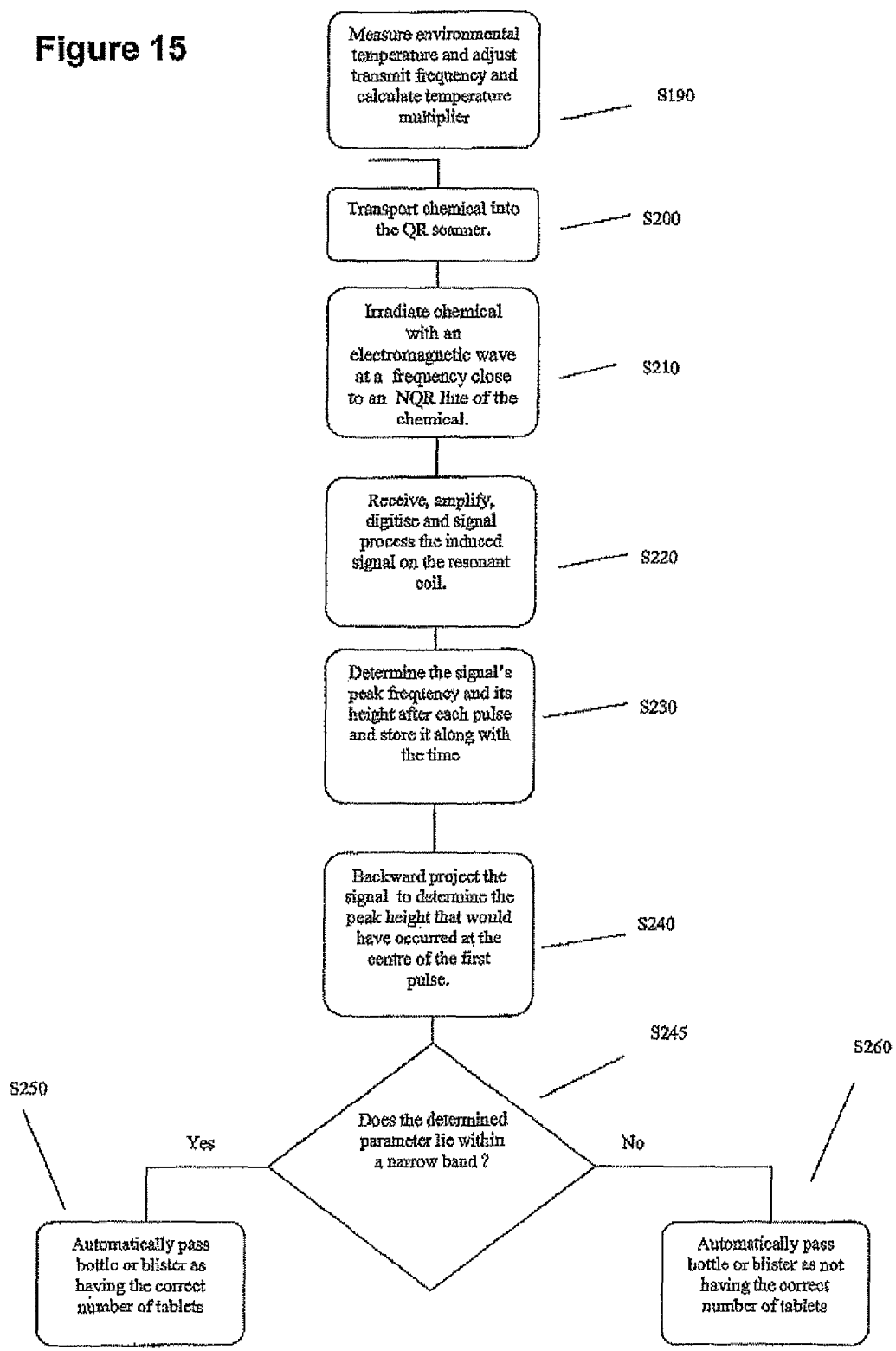
FIG. 15 is a flow chart showing the general process followed for measuring an NQR signal of an unknown number of tablets to identify the correct number in a container in accordance with the second embodiment.

The next stage of the process is to measure the QR signal from a container that contains an unknown number of tablets. The general process that is followed is shown in FIG. 15.

As before the temperature of the surroundings or the sample are measured S190 and the sample is moved into the QR scanner via conveyor belt S200. There the sample is irradiated with an AC magnetic field causing a QR signal to be generated S210. After amplifying, filtering, apodising, applying the temperature multiplier and Fast Fourier Transforming the resultant signal after each pulse S220, the peak heights are stored S230 and then backward projection is used to determine the peak height at the centre of the first pulse S240. This value is used to determine whether it lies within the bounds set during the calibration phase S145. If it does lie within the bounds of the calibration phase then it is deemed to have the correct number of tablets S150, otherwise it is deemed to have the incorrect number of tablets and it is subsequently rejected S160.

Figure 16:
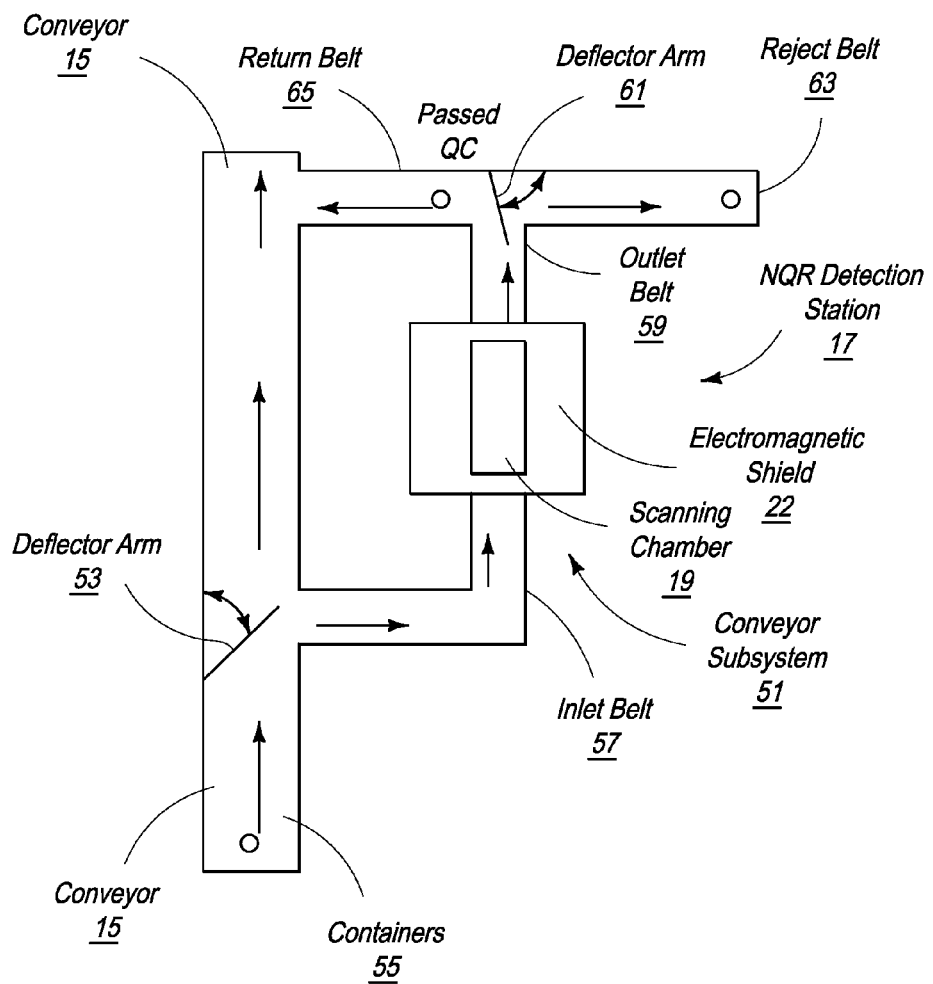
FIG. 16 is a schematic diagram showing the side-line conveyor system and detection station therein as described in the second embodiment.

As shown in FIG. 16 of the drawings, the NQR detection station 17 is disposed in a side-line conveyor sub-system 51, which operates in parallel to the main conveyor 15. The sideline conveyor sub-system 51 includes a deflector arm 53 for controllably deflecting containers 55 off the main conveyor 15 in either a random or predetermined manner according to a quality control program operated in conjunction with the production line process. The deflected containers are conveyed along an inlet belt 57 of the sub-system 51 and into the NQR detection station 17 where the QR coil and probe is located. The maximum rate that containers 55 can be deflected by the deflector arm 53 and conveyed along the inlet belt 57 is determined by the speed of the QR scan time, which is typically much slower than the rate at which containers would be dispensed out of a container packaging machine (not shown) feeding the main conveyor 15.

The scanning chamber 19 of the detection station 17 is differently shaped from that of the preceding embodiment, so that the circumscribing coil therein more closely corresponds to the size of the containers passing therethrough, as opposed to the blister packs of the preceding embodiment. The transmit-receive coil located within the scanning chamber 19 has a highly homogeneous magnetic field pattern. The reason for this requirement is that the signal derived from a QR coil is dependent upon the applied field strength, i.e. the stronger the field, the stronger the signal. Additionally, the container 55 may end up in the middle of the coil, which is the preferred option, or could lie close to one end of the coil; hence to achieve a reproducible signal strength it is necessary to have a field pattern that is homogeneous in field strength throughout the coil. Therefore, instead of adopting a single-turn flat resonant coil, as used in the previous embodiment, a birdcage coil is used because of its high field uniformity compared to other coils. As in the preceding embodiment, the birdcage coil is surrounded by an electromagnetic shield 22 to isolate the scanning chamber 19 from electromagnetic noise.

The particular configuration of the scanning chamber and coil is arranged to situate containers therein so that the magnetic field lines produced by the coil are orientated to be mostly parallel to any metal surfaces, such as the lid of the container or the aluminium foil seal at the top of the container, to prevent field inhomogeneities within the coil. As described in the previous embodiment, if the field impinges upon an orthogonal metal surface, then eddy currents are induced in the metal surface, which oppose the applied field and thus destroy this field and the sensitivity of the coil in this area. When measuring containers of tablets, most tablets will lie well away from the metal surface, which will limit the effect of the metal surface at the top of the container. Another way of even further limiting this problem is to analyse fully plastic containers without any sealing foil at the top of the container.

A container 55 is temporarily disposed within the detection chamber, and after being scanned and analysed in the prescribed manner, is exited therefrom along an outlet belt 59 and passed to another deflector arm 61 that deflects the container either along a reject belt 63 to a reject depository or a return belt 65 to return the container to the main conveyor line 15, depending upon the outcome of the analysis. Thus if the analysis reveals that the tablets within the scanned container do not meet the prescribed quality control standards incorporated into the analysis program performed by the analysing means of the signal processing unit 31, then the container is rejected and directed to the reject depository. Alternatively, if the tablets do meet the prescribed quality control standard, then the container is passed and returned back to the main conveyor line via the return belt 65.

The third embodiment is substantially the same as the second embodiment, except that instead of applying the FFT to the digitised signal, the maximum peak of the time domain response for each echo is recorded and these are used to project back to the centre of the first pulse. This value at the CFP is used determine the number of tablets within the bottle.

The fourth embodiment is substantially the same as the second and third embodiments, except that rather than determining the number of tablets in a container, the backward projection technique is used to determine how much of a particular chemical is present in the container. An example of where this is useful is during manufacture of chemicals that are mixed with what are known as "excipients". These materials serve a number of functions, which include:

(i) Binding
(ii) Disintegrators
(iii) Fillers
(iv) Lubricants
(v) Glidants
(vi) Compression Aids
(vii) Colours
(viii) Sweeteners
(ix) Preservatives
(x) Suspension/Dispersing Agents
(xi) Coating Agents
(xii) Flavours
(xiii) Printing Inks Typical excipients include magnesium stearate and calcium stearate. It is important during manufacture that the excipient is well mixed with the chemical being analysed, because if the distribution of drug is too low, then an underdose wilt occur; or if the dose is too high, then a over dose will occur. The present embodiment offers a way of checking that the mix has occurred well in the sample by measurement of the frequency response and determining how much chemical is present.

The fifth embodiment is similar to the first and second embodiments, except that it uses a different technique than the ETE described in the first embodiment by which the frequency distribution of the NQR signal that provides a measure of the crystal quality, homogeneity, purity and the mechanical handling to which the tablets have been subjected, may be generated, and the long multiple pulse echo train with phase cycling of the second embodiment. Moreover, the present embodiment makes use of a two-dimensional (2-D) Fourier transform technique at the expense of a significant increase in the measurement time. Furthermore, in order to accommodate this increased measurement time, the present embodiment adopts the side-line quality control system of the second embodiment instead of the in-line quality control system of the first embodiment, which can accommodate longer measurements than the in-line system, albeit at a lower ratio of quality checked containers per unchecked containers, but which is still far greater than quality checking techniques used in the art at present.

Figure 17:
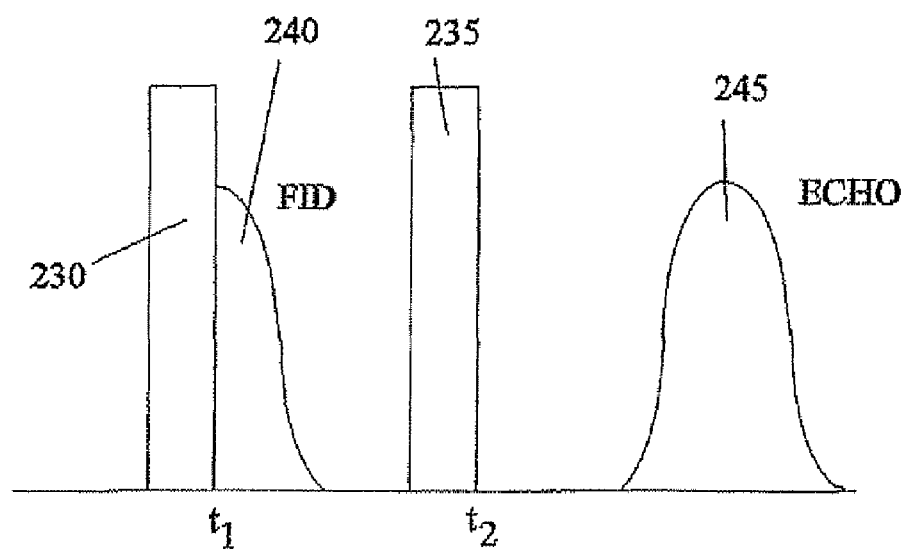
FIG. 17 is a signal diagram showing an amplitude-time graph of the two pulse sequence described in the fifth embodiment.

The present embodiment employs the simplest way of applying the 2-D Fourier transform technique by using a two pulse sequence in which the preparation pulse consists of a single pulse, in width (although this can be varied), followed by a variable period $t_1$ and then a second pulse, of width 180° (although this can also be 90°), followed by a period $t_2$, as shown in FIG. 17, in which the response signal is received.

The receiving and processing means applies a 2-D Fourier transform with respect to both $t_1$ and $t_2$ to generate a 2-D spectrum in which $\omega_1$ displays the true or homogeneous line shape and $\omega_2$ the broadened or inhomogeneous line shape, which is a convolution of the former with the static frequency distribution, due possibly to impurities or disorder in the structure. Deconvolution of one with the other gives the static distribution, which is used by the analysing program as a measure of crystal quality, homogeneity purity and/or the mechanical handling to which the tablets under the analysis have been subjected.

The sixth embodiment is substantially the same as the preceding embodiment, except that it uses a different technique for generating a frequency distribution of the NQR signal than the ETE and the 2-D Fourier transform technique described in the preceding embodiments, thereby providing an alternative measure of the crystal quality, homogeneity, purity and the mechanical handling to which the tablets have been subjected.

In the present embodiment, a two-frequency NQR method is used, which is applicable when two transitions of a given nucleus are connected, i.e. have an energy level in common, to derive information on the angular distribution of inhomogeneities in the EFG. This method is used to produce both polarisation and coherence transfer.

In order to produce coherence transfer, the pulse generating and transmitting means of the present embodiment generates a pair of 90° pulses separated by a variable delay $t_1$, and applies it to one transition $\nu_1$ followed by a 90°-τ180° pulse pair at the second connected transition of frequency $\nu_2$, the first component following either immediately before or after the second pulse at the first frequency $\nu_1$, and the signal being detected at $\nu_2$, a time $t_2$ following the 180° pulse. A double Fourier transform with respect to $t_1$ and $t_2$ gives a 2-D spectrum correlating the two transitions $\nu_1$ and $\nu_2$, from an analysis of which the individual broadening components of the EFG tensor, $\Delta q_{xx}$, $\Delta q_{yy}$, $\Delta q_{zz}$ can be derived.

The analysis program follows an algorithm whereby the differences between these broadening components are used to discriminate between different broadening mechanisms in the particular sample of the tablets being analysed. Equal values are expected for the disordered or amorphous phases in which the probability distribution functions along the x, y, z principal axes of the EFG tensor are very similar or identical. Anisotropy in the broadening components may indicate impurity or defect broadening, in which these features occupy specific sites in the crystal structure of the bulk material and may therefore perturb $q_{xx}$, $q_{yy}$, $q_{zz}$ to differing extents.

These differences are compared against a threshold reference or range prescribed for the particular pharmaceutical under analysis, in this case furosemide, with any measured difference exceeding the threshold or range resulting in the container of tablets causing the same to be rejected, and an operator alarmed.

The two-frequency NQR method lends itself to being used to help identify that a particular pharmaceutical has come from a given batch or a particular manufacturer. In this arrangement, a known defect or impurity with a predetermined inhomogeneous frequency distribution, which can positively identify a chemical substance using NQR, is deliberately introduced into the manufacture of that substance.

In this manner, during chemical analysis of a specimen of that substance using the two-frequency method described above, the specimen can be positively identified as to whether it has come from a particular batch or manufacturer, depending upon the matching of the derived frequency distribution with a reference value.

The seventh embodiment is substantially similar to the preceding embodiment, except that it employs the use of a three-frequency NQR method for determining the frequency distribution of the specimen being analysed in lieu or in addition to the two-frequency method.

In the three-frequency method, excitation at the two lower frequencies of $^{14}$N, $\nu_0$ and $\nu_-$ generates a signal at the highest frequency $\nu_+$ without any pulse being applied at that frequency, so there is no dead-time problem. Compared with results obtained using the two-frequency method, there is much more information on line broadening, e.g. distinguishing between correlated and uncorrelated effects. However, there is a loss in signal intensity and so three sets of orthogonal RF coils are required.

Figure 18:
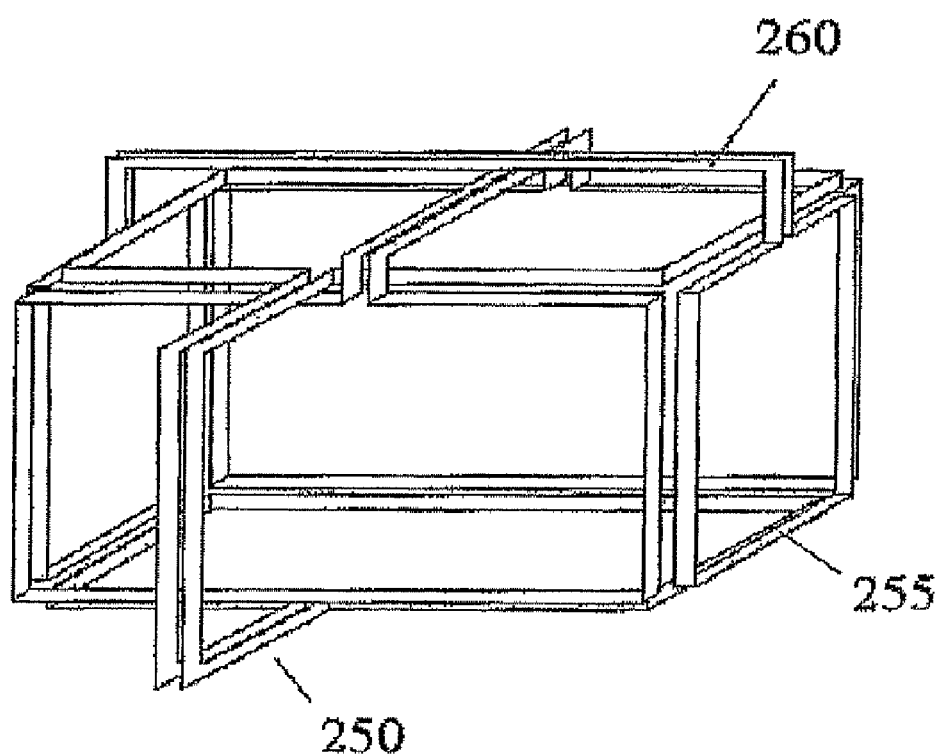
FIG. 18 is a schematic diagram showing the three sets of coils as described in the seventh embodiment.

Accordingly, the present embodiment involves the arrangement of three sets of orthogonal RF coils, configured as shown in FIG. 18 of the drawings, and the analysing program is modified to perform a three-frequency NQR analysis to obtain the frequency distribution of a container of tablets conveyed to the NQR scanning station.

In view of the complexity of the three coil arrangement required, the preferred implementation of the present embodiment is as a further check on quality control to supplement an initial check performed according to any of the preceding embodiments, rather than as a primary check replacing the method used in the preceding embodiments for same.

The eighth embodiment is substantially similar to the second embodiment, but provides for an alternative method for measuring line-width to reliably identify pharmaceuticals having poor crystallinity or impurities in them. The general process followed is:
 (i) Determination of environmental temperature prior to calibration process.
 (ii) Calibration of the QR coil.
 (iii) Determination of environmental temperature prior to the measurement process.
 (iv) Measurement of a QR line-width of the contents of a container using a reproducible technique.
 (v) Determination of whether the signal's line-width lies within the correct bounds for the required crystallinity.

In this embodiment the line-widths are determined to form a measure of the crystallinity of the sample being analysed.

The requirements for a technique that produces reproducible line-widths are similar to those of the second embodiment. These requirements include that the temperature is measured, the field within the coil is homogeneous, and Q switching; and all of these are performed in this embodiment.

Figure 19:
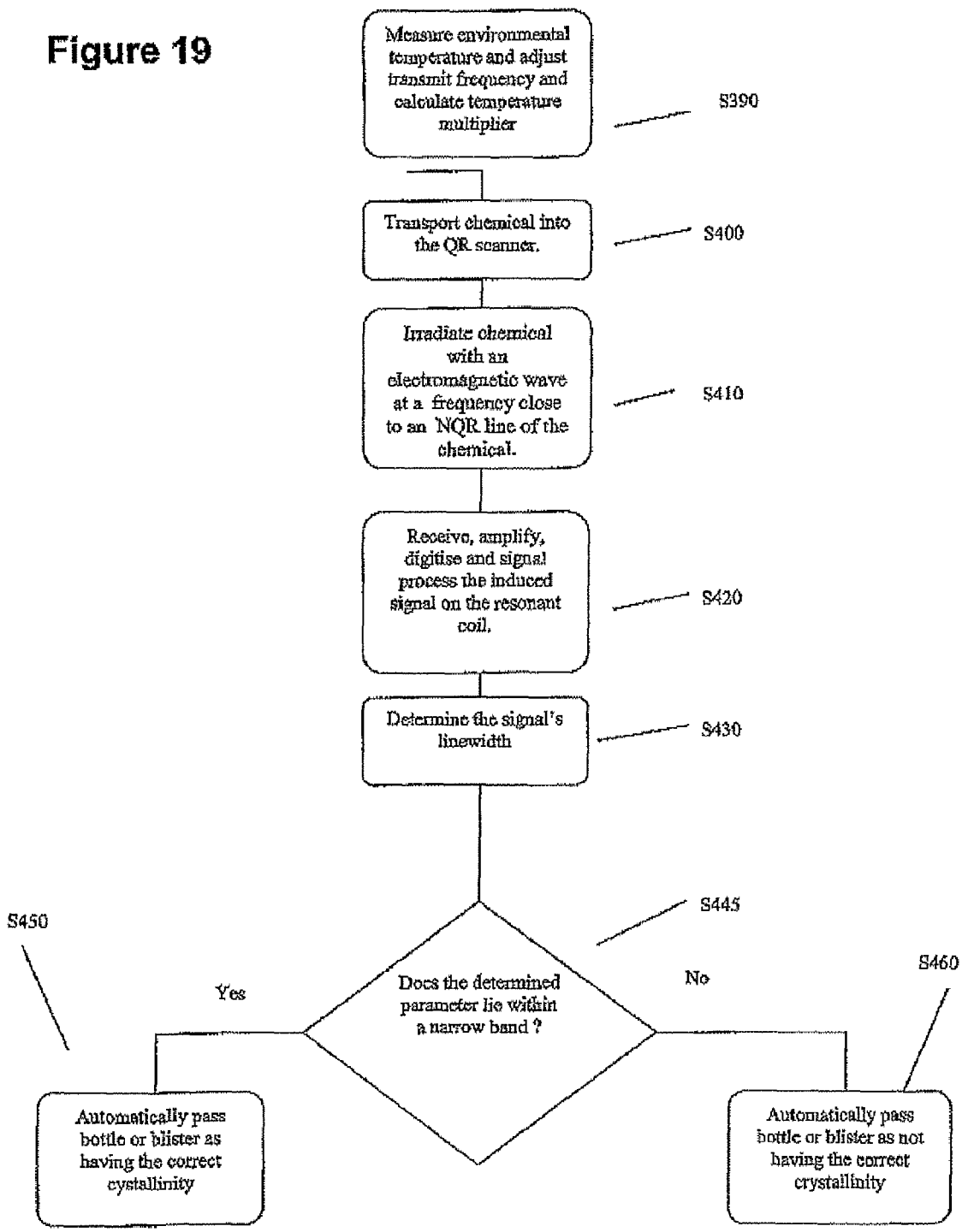
FIG. 19 is a flow chart showing the process followed for determining the line-width of a pharmaceutical under test, after it has entered the scanning chamber in accordance with the eighth embodiment.

The pulse sequences used, however, are different. The pulse sequences used are any of those as described in the first embodiment. Hence, in this embodiment, firstly the calibration is performed by measuring the temperature, to know exactly where the NQR frequency line will occur. Then at least two, preferably more, calibration samples are measured: some of which have poor crystallinity and some of which have the required crystallinity. All of these samples are measured in the NQR spectrometer using the pulse sequence techniques described in the first embodiment and the bounds for line-widths are determined. These are then used as detection criteria to determine if the substance meets the quality control requirement for crystallinity. Next a sample is moved into the QR coil and the process as shown in FIG. 19 is performed.

Firstly, the environmental temperature is measured and used to adjust the transmit frequency S390. Then the sample is moved into the coil S400, scanned S410 and processed S420 to determine the line-width using a pulse sequence technique S430. If the line-width satisfies the required crystallinity criteria S445, then the sample is passed as having satisfied the quality control requirements S450 or rejected as not having satisfied the quality control requirements S460.

The ninth embodiment is substantially the same as the second embodiment, but additionally involves using the NQCC and asymmetry parameters to determine which chemicals are present in the particular pharmaceutical under test.

During production processes that involve reacting various organic chemicals together, typically more than one compound can be produced. Hence, it is necessary to monitor what compounds the production process is producing and whether the desired chemical(s) are being produced in sufficient quantity throughout the process. It is also necessary to ensure that the raw inputs are the correct substances.

To expedite the in-line analysis of the present embodiment, prior small-scale laboratory experiments are performed to determine what compounds can be produced if the chemical processing proceeds down the wrong reaction path. For instance, if the reaction vessel is at a slightly higher temperature than it should be, then more of an undesired chemical might be produced compared to a desired chemical.

As the desired/undesired compounds will be well known in advance of the full scale production process commencing, the NQR frequencies and parameters of the both types of chemicals are measured ahead of production, and the quality control system perfected to detect not only the desired chemical, but other undesired chemicals.

Some compounds produced by the production process will have very similar structures. For instance, the reaction and drying process may generate isomers and polymorphs. Polymorphs have the same chemical formula but have a different crystalline structure. In the United States it is a requirement that the polymorph produced is labelled on the outside of the container. Isomers also have the same chemical formula, but some bonds are transposed, i.e. they occur in different places.

If it was simply was the case that where the frequency lines occurred gave a clear indication of what chemical was present, this would be sufficient in terms of quality control. This is probably true when frequency lines are widely separated in frequency and there is no possibility of overlapping lines occurring. However, because polymorphs and isomers typically have NQR frequencies which occur close to each other in the frequency spectrum and temperature movements can cause these lines to drift, interpretation of the chemical present is made difficult. This is further complicated by the fact that similar compounds will produce similar intensities after being exposed to the same pulse sequence.

The present test addresses these difficulties to unequivocally identify the compounds present by combining the frequencies to calculate NQCC and asymmetry parameters. If this is still not enough to distinguish the compounds apart, the relaxation times are then determined and analysed to determine the chemical present.

To calculate the NQCC and asymmetry parameters for any one chemical, such as in the furosemide tablets of the present embodiment, at least two frequencies are required. Using the base equations in (1) for the $v_x$ and $v_y$ lines it is possible to calculate the NQCC and asymmetry parameters ($\eta$) by combining the three equations in (1) to produce two new equations:

$$NQCC = \tfrac{2}{3}(v_x + v_y)$$

and $$\eta = 3(v_x - v_y)/(v_x + v_y)$$

(It is possible to produce equations in terms of $v_z$ if required).

Hence, to calculate the NQCC and asymmetry parameters, prior knowledge about the frequencies at which the lines of both the desired and undesired chemicals determined ahead of production in the laboratory or through looking at NQR frequency tables in scientific journal articles or books such as the Landolt-Bornstein, Numerical Data and Functional Relationships in Science and Technology, New Series, Group III, Volume 20, Nuclear Quadrupole Spectroscopy Data, Subvolume A, Springer-Verleg, New York, 1988 which contains NQR frequencies for a variety of quadrupolar substances.

Once the NQR frequencies of desired and undesired substances are known, the coil is arranged to scan specific frequencies by retuning the coil. The retuning is achieved by adding in capacitance into the resonant circuit of the QR scanner. The QR scanner then scans sequentially all of the lines deemed that should be searched for, in order to detect the desired and undesired NQR frequency lines. Depending on the chemical being produced, and because some lines can occur close to each other, it is possible that the one scan will excite more than one line and thus save the need for additional retuning and scans.

The steps involved in the present test include.
(i) Predetermining the frequencies at which the NQR frequency lines of the desired and undesired compounds will occur. Additionally, determining the relative signal strengths of each individual line at these frequency lines. Predetermining which pulse sequence and pulse sequence parameters that should be used to detect all lines.
(ii) Measuring the environmental temperature (this is described more in the second embodiment).
(iii) Calibration of the expected relative signal strengths of the desired/undesired chemicals in a 'good' sample (also discussed in more detail with respect to the second embodiment).
(iv) Measurement of the peak height of two of the frequencies for at least one compound contained within a container containing an unknown chemical.
(v) From the measured frequencies, determining the NQCC and asymmetry parameters.
(vi) Determining if the values agree with the desired compounds sought or undesired compounds.
(vii) On the basis of (vi), accepting or rejecting the container as having passed or not passed quality control requirements.

In the first step, the frequencies and relative strength of all the lines that could be detected during the NQR analysis are determined. These lines include all desired and undesired chemical frequency lines. The pulse sequences and pulse sequence parameters which are best optimised to detect these lines are also determined.

The second step involves measuring the temperature of the surroundings and/or the sample. As before, this measurement is performed to correctly transmit pulses close to the resonant frequency of the substances of interest, but also to know more accurately which lines detected belong which chemical for the purposes of calculating NQCC and asymmetry parameters.

To perform the calibration step, multiple known samples containing the desired/undesired chemicals in separate containers are individually scanned in a QR scanner. Once within the coil the system is sequentially tuned to the first desired chemical line, the second desired chemical line, a first undesired chemical line, a second undesired chemical line and so on for as many desired/undesired chemicals as there could be in a sample. After each retuning, a pulse sequence tailored to stimulate that particular line or lines is transmitted to the coil via an amplifier. In each case this pulse sequence stimulates the quadrupolar nuclei.

After each pulse has finished a Q switch is used to drain off the remaining transmit pulse from coil and then the acquisition of the signal begins. During the acquisition period the signal is amplified, sent through a mixer to create quadrature signals and these signals are sampled by an ADC. The digital signal sampled after each pulse is accumulated into one array and sent to the signal processing routine. In this routine the digital signal is filtered, thresholded, apodised, and Fast Fourier Transformed. In the frequency space the peak signal frequencies are recorded for each scan, forming an array of frequencies and their corresponding intensities. Using the expected frequency values on the basis of temperature, these frequencies values are combined using the above equations to produce NQCC and asymmetry values. Then these values are stored for future use.

Figure 20:
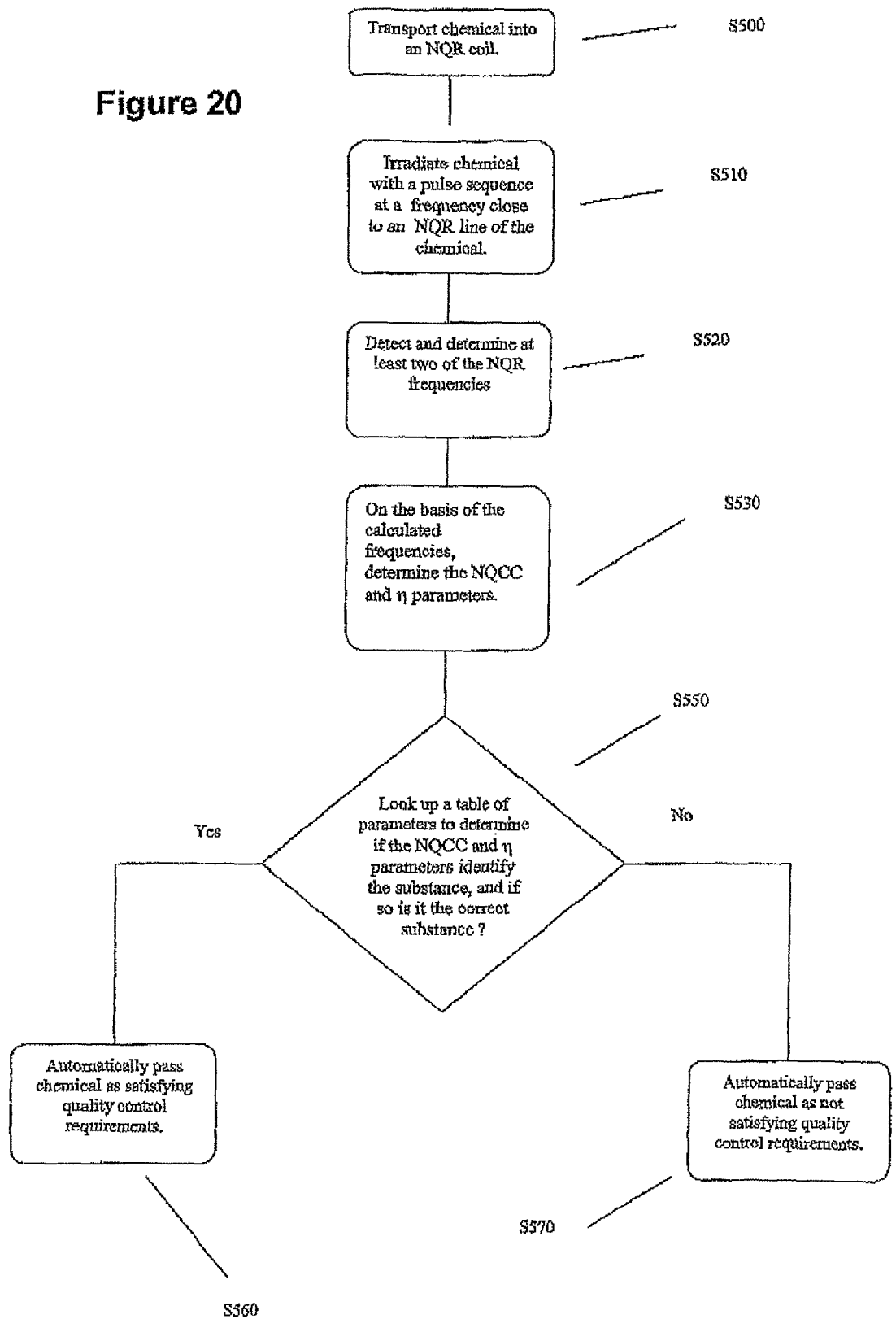
FIG. 20 is a flow chart showing the process followed for identifying the pharmaceutical under test, after it has entered the scanning chamber in accordance with the ninth embodiment.

As shown in FIG. 20, a container containing an unknown chemical composition is then moved into the QR scanner via a conveyor belt S500 and analysed with the same procedure S510 and S520 except that after calculating the NQCC and asymmetry parameters S530, these are compared to the previously stored values to determine which substance or substances are present S550. If the desired substance is present and the undesired substance's signal intensity lies below a specified threshold the chemical is passed as having satisfied the quality control requirements S560. If not, the chemical is rejected S570.

The threshold used to determine whether the undesired substance is present may be set at some level at which a low false alarm rate is produced, such as three or four standard deviations above the noise in the frequency spectrum surrounding the undesired peak of interest.

In an alternative to this embodiment, rather than calculate the NQCC and asymmetry parameters the frequencies detected and the expected frequencies on basis of temperature are used to identify the compounds found. With accurate measurements of temperature the frequency lines for all the substances should be well known and be relatively easy to identify, except when the peaks overlap or lie close to each other, in which case the NQCC and asymmetry parameter method is superior. The signal intensity pattern at the various frequencies will also help to identify the substances present.

This embodiment not only has utility with respect to detecting the presented of unwanted chemicals or compounds, but it also may be adapted to identify the desired compound as one polymorph and the unwanted compound as an undesired polymorph.

Further still, the desired compound may be identified to be one isomer and the second substance is an undesired isomer.

In another alternative for this embodiment, if it is difficult to determine which compound is present after the NQCC and asymmetry parameters have been determined the relaxation time of the various lines detected are determined and compared to values determined during step (i) to identify the compounded detected.

The tenth embodiment is an alternative to the preceding embodiment, whereby the relative signal strengths at the frequencies of a desired and a undesired compound are measured and if the undesired/desired signal strength ratio exceeds a certain value then the sample is rejected.

The eleventh embodiment is substantially similar to each of the preceding embodiments, except that the coil arrangement is portable. Accordingly, in this embodiment, rather the sample being conveyed to the coil, the coil is brought to the sample and the sample is placed within the coil by an operator for quality control testing.

In the process of production, because of the high costs of pharmaceuticals, copies are often made by other parties who then attempt to sell the pharmaceutical as genuine product. To counter this problem a chemical is tagged by adding one or more benign quadrupolar substances to the chemical, which can be used to identify the true producer of the chemical. By performing this operation drug stores can ensure that the product they are buying is genuine product produced by the manufacturer identified on the packaging. The quadrupolar substance(s) added to the chemical do not interfere with the absorption of the drug within the patient, nor do they alter the chemistry of the drug. They are also non harmful to the patient.

Hence in a twelfth embodiment of this invention, which is substantially the same as each of the preceding embodiments, the lines of the desired compound searched for include the tagged substance used as a signature to identify that the product is genuine.

The thirteenth embodiment is substantially the same as the second embodiment, except that it involves using polarisation enhancement to reliably increase the signal strength or decrease waiting times, allowing for faster measurement.

An inherent problem with some compounds is that the number of quadrupolar nuclei in the sample being analysed is relatively low. For example, in the aforementioned drug Atenolol ($C_{14}H_{22}N_2O_3$), only two out of the 41 atoms in the molecule are nitrogen. The result of this is that the signal strength measured will be weak, because the relative number of nitrogen atoms is low. As a result of the signal strength being poor, the time taken to measure the NQR signal in order to gain enough signal in the signal averaging process, is also very long. To overcome this deficiency, polarisation enhancement is used to polarise the nuclei before measurement begins, so as to increase the signal strength.

Another inherent problem with some NQR measurements is that substances which have a long $T_1$ relaxation time take a long time to recover after a pulse sequence has been applied. Such large relaxation times mean some substances cannot be rescanned until several minutes have elapsed. Cross relaxation methods offer a solution to overcome this problem. By exposing the substance to a DC magnetic field in between pulse sequences, the energy stored within the lattice structure is drained, allowing a reapplication of the pulse sequence immediately and thus shortening the measurement cycle.

To generate cross-relaxation (CR) and cross-polarization (CP) effects in a targeted substance within a pharmaceutical being quality tested, the detection algorithm essentially includes the steps of:

applying a DC magnetic field to the pharmaceutical sample under test, and
adiabatically removing DC magnetic field from the sample;

in some combination with:

applying a sequence of RF pulses to the sample, and
detecting response signals from the sample.

Thereafter signal processing of the response signals is undertaken to detect an NQR signal indicative of the targeted substance if present.

The order and number of repetitions of each step in the detection algorithm can be different for different tasks, depending on whether CP (also known as polarization enhancement (PE)) or CR is used.

In the case of CP/PE, the actual sequence of steps involves:

applying a DC magnetic field to the sample,
adiabatically removing DC magnetic field from the sample, to reach some energy level where the polarization is transferred to the quadrupolar nuclei,
applying a sequence of RF pulses to the sample,
detecting response signals from the sample,
signal processing the response signals to detect an NQR signal indicative of the targeted substance if present.

In the case of CR, the sequence of steps is performed, more or less, in reverse, involving:

applying a sequence of RF pulses to the sample,
detecting response signals from the sample,
adiabatically applying and removing a DC magnetic field to cause energy in the quadrupolar system to be drained into the proton system, allowing a rapid repeat of the next NQR pulse sequence as the spin-lattice relaxation time $T_1$ has been effectively reduced,
applying another sequence of RF pulses to the sample, and
signal processing the response signals to detect an NQR signal indicative of the targeted substance if present.

Using CP or CR improves the results that can be achieved from using a multiple or combination of pulse sequences, without detracting from commercially acceptable detection times, than would otherwise be the case. More specifically the use of CR and CP produces a significant reduction in the waiting time in between pulse sequences and improved signal-to-noise ratio (SNR).

As previously described, this waiting time is required for the effective detection of NQR signals in substances using multiple or combination sequences of pulses.

The CP and QR techniques are particularly effective for the detection and identification of substances containing at least two kinds of spin-system: quadrupolar nuclei (normally nitrogen $^{14}N$) and nuclei with a magnetic moment (normally protons). The theory behind the CP/PE and CR will now be described in more detail below.

Figure 21:
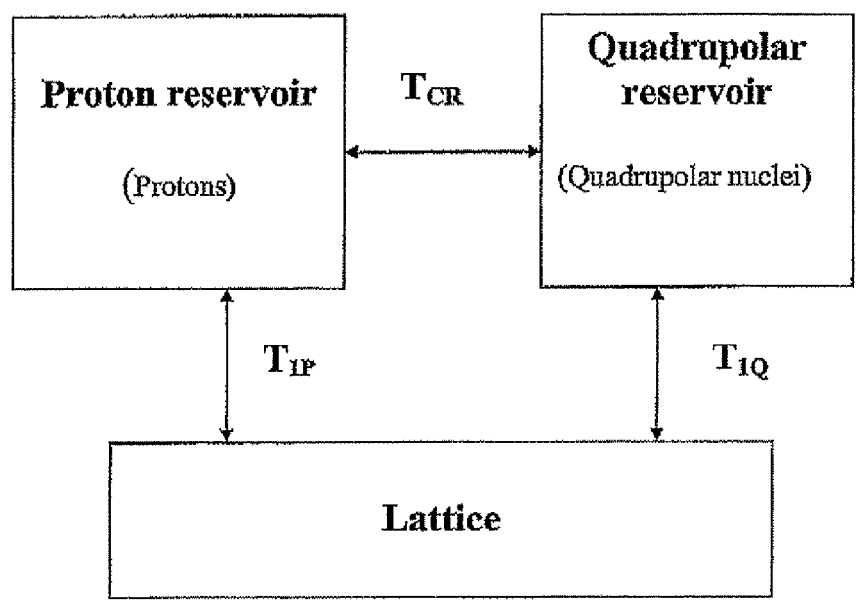
FIG. 21 is a schematic diagram describing the connection between the Q and P reservoirs and the lattice, as referred to in the thirteenth embodiment.

The quadrupole reservoir Q of abundant quadrupolar nuclei and the proton reservoir P of abundant protons are connected with the lattice and this connection is characterised by the spin-lattice relaxation times $T_{1Q}$ and $T_{1P}$ respectively. The connection between Q and P reservoirs can be established using special experimental techniques and is characterised by the cross-relaxation time $T_{CR}$. The diagram describing the connection between the two reservoirs and the lattice is shown in FIG. 21.

The enhancement of the NQR signals can be achieved by using the cross-polarization (CP) effect. The underlying physical process constituting the CP effect is to bring the nuclei in the P reservoir, occupying NMR energy levels created by a small DC magnetic fields to the same energy difference as that of an NQR transition, so that an exchange of polarization can occur between the P and Q reservoirs. The separation in NMR levels can be controlled by the strength of an applied DC magnetic field, while the NQR energy levels are mainly determined by the bonding environment. In this process it is possible to increase the polarization of the NQR system through the CP from the NMR levels.

Figure 22:
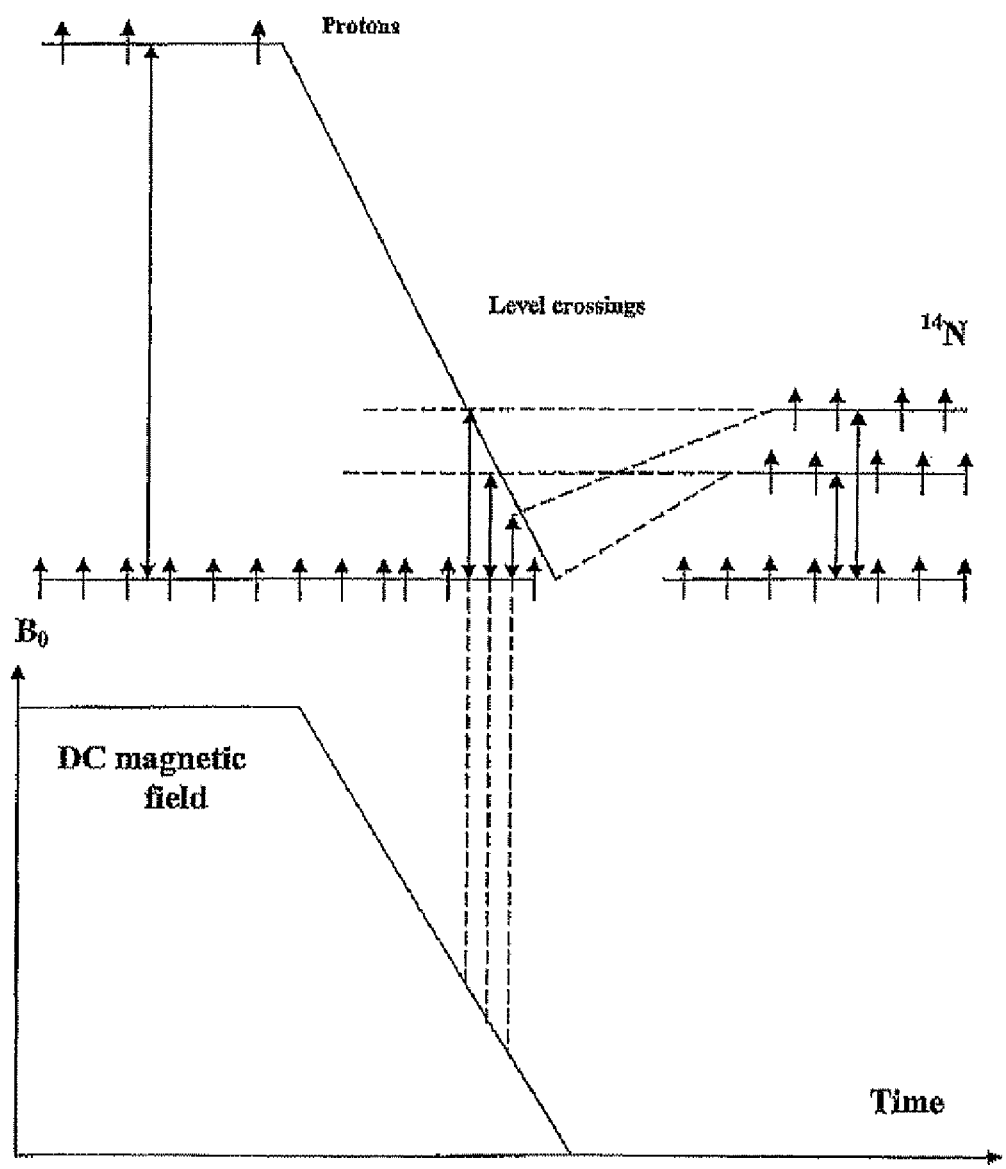
FIG. 22 is a schematic diagram showing the energy level separations with respect to time for proton polarisation using the CP method, as also described in the thirteenth embodiment.

For the CP method, a basic approach is to initially polarize protons, which are more abundant in a sample in a static (DC) magnetic field, so that the proton energy levels have much greater separation than the NQR levels. Given time to equilibrate, these proton levels will have relative occupation numbers determined by the Boltzman distribution. The relative population difference between the two proton levels, hence polarization, will correspondingly be much greater than would be the case with the NQR levels. By reducing the DC magnetic field adiabatically the proton level splitting is reduced such that the proton and quadrupolar energy level separations equalise allowing a transfer of polarisation. (see FIG. 22). This results in a net polarisation from protons to the quadrupolar nuclei.

This can also be explained through the concept of spin temperatures, where energy flows from the "hot" quadrupolar spin-system to the "cold" proton spin-system to "cool" the quadrupolar spin-system.

By applying conventional pulse detection techniques soon after removing the DC magnetic field, the NQR response can be improved by virtue of the ratio of the proton NMR to NQR frequency, provided the proton reservoir is sufficient to cool the quadrupolar system to the proton spin temperature.

A feature that is noteworthy is that unlike conventional NMR, the increase in signal is not critically dependent on the uniformity of the DC field. Removing the uniformity requirement lowers the technology cost considerably and allows diverse applications compared to NMR alone.

It has been discovered, pursuant to the best mode, that for the efficient detection of NQR in a sample, the cross-relaxation (CR) effect can also be used, which takes place between the Q and P reservoirs.

Furthermore, it has been discovered that the PE NQR technique is also applicable in the case of multi-pulse sequence NQR and can be used in combination with the CR technique.

In any of the preceding embodiments, the signal strength is increased and the waiting times between pulse sequences are reduced by exposing the sample to a DC magnetic field and then performing the NQR measurement.

Figure 23:
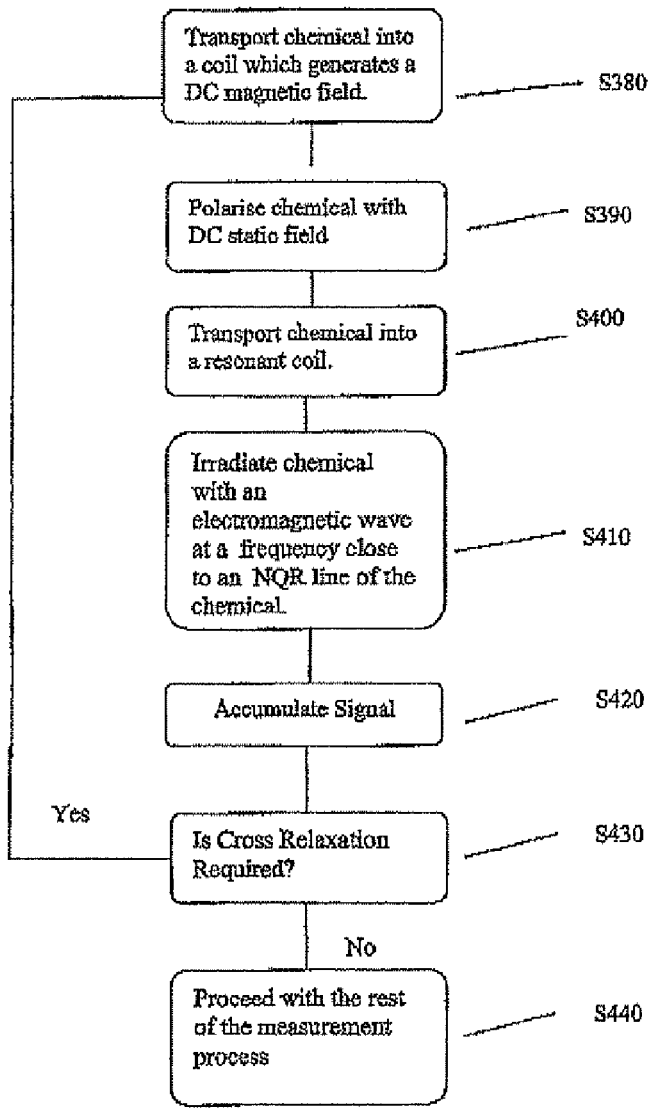
FIG. 23 is a flowchart showing the process followed for quality control using polarisation in accordance with the thirteenth embodiment.

Hence in the present embodiment, as shown in FIG. 23, a sample is transported into an auxiliary coil, which generates a D C magnet magnetic field S380. This auxiliary coil in one arrangement is spaced laterally away from the resonant coil or in another arrangement of the embodiment, surrounds the resonant coil-shield system, as DC magnetic fields penetrate metals such as copper sheet without loss of intensity. Whilst under the influence of the DC magnetic field the atoms are polarised S390. After being polarised, the sample is moved into a resonant coil system S400 where the NQR measurement is performed S410. Then the signal that occurs after each pulse in the pulse sequence is accumulated into an array for later processing S420. At step S430, if cross relaxation is required to overcome a substance which has a long $T_1$ relaxation time, the sample is moved back into the DC magnetic coil (if transportation is required), where the DC field drains energy out of the quadrupolar system back into the proton system, allowing the quadrupolar system to be re-energised. In step S440 the normal processing then continues depending upon which of the previous embodiments polarisation and cross relaxation is used in conjunction with.

As described in the second embodiment and as shown in FIG. 16, the system incorporated a side conveyor to the main line. The reason why the NQR scanner has to be located in a side line is that the NQR scanner cannot normally scan containers fast enough to keep up with the rate at which they are being produced by a blister pack or container dispensing machine. One fortunate advantage in NQR that can be exploited is parallel and serial scanning of many containers at once. Dramatic increases in throughput are achievable by using such a system. The fortunate part about NQR scanners for scanning small containers is that they are relatively inexpensive and the cost of placing many scanning units side by side is not beyond the cost of setting up a production plant, given $500 million or more can be spent in building such a production plant.

Accordingly, the fourteenth embodiment is directed towards an NQR scanning system comprising a plurality of scanning units of the type described in any one of the preceding embodiments, wherein each scanning unit has its own coil, capacitors, shield, mixer, high power amplifier and small signal amplifier, and links into a simultaneously sampling high channel ADC board for receiving the signals from all of the coils at once. A single computer controls the entire operation, incorporating the control and signal processing unit for each scanning unit.

Hence in this embodiment separate containers are moved along a conveyor belt into both serial and parallel QR scanners. These scanners are filled with one container at a time and the scanning operation takes place, simultaneously scanning many containers at once. The results from each individual scanner are used to determine if the container within is kept or is passed through the rejection line.

Figure 25:
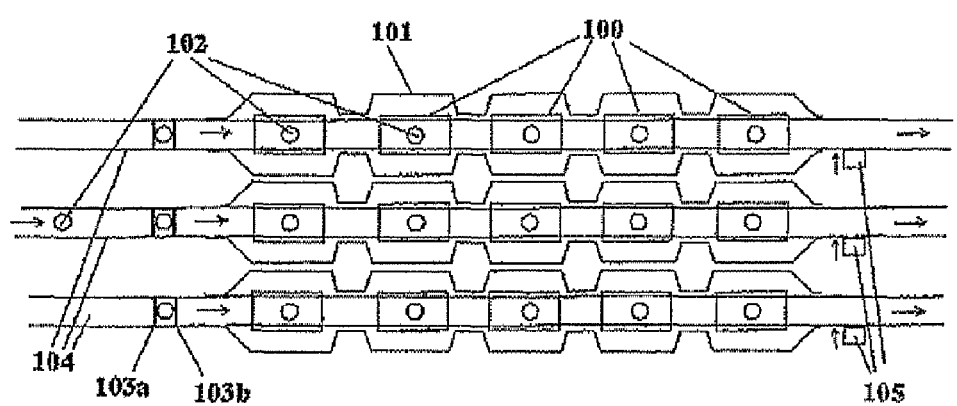
FIG. 25 is a schematic diagram showing parallel and serial QR scanner and conveyor configurations for simultaneously checking containers to increase throughput for quality control procedures as described in the fourteenth embodiment.

The arrangement is better illustrated in FIG. 25, whereby containers containing pharmaceutical 102 are moved along conveyors 104 into a multitude of QR scanners. These scanners have within them coils 100 and are surrounded by a shield 101. Two problems which occur with this design are firstly the fact that bottle-type containers tend to easily fall over and secondly there is a need to equally space the bottles such that they lie within a QR scanner when they are scanned.

The first problem is solved by the provision of support rails either side of the conveyor to give support to the bottles as they pass. The support rails run underneath the neck of the bottle, preventing the bottle from falling forwards or backwards. The support rails and the conveyor are made of a plastic or similarly nonconductive material to prevent them from interacting with the magnetic field of the QR scanners.

The second problem is solved by the use of gates 103a and 103b. As a bottle reaches gate 103a it is detected by an optical sensor (not shown). If there is no bottle in between gates 103a and gates 103b, then gate 103a opens and allows the bottle to pass until it hits gate 103b where it is held. Gate 103b opens when the distance between it and the previous bottle is approximately the same distance as between the centre of any two coils in the coil cluster.

This process is continued until all the coils are filled with bottles to scan. Then they are scanned simultaneously and the signals are transferred back to the centralised computer (not shown), which analyses the results and determines if the bottles satisfy the quality control requirements. If any of the bottles fail the quality control tests then they are rejected by the use of rejecting arm 105, which comes across the belt and deflects the unwanted bottles out of the conveyor.

The fifteenth embodiment is substantially the same as the second embodiment, except that the system includes provision for detecting metal contamination and QR signals using the one apparatus.

In the production process, metal contamination by pieces of broken machinery, filings and other metal pieces can inadvertently end up in the final product. Such metal contamination is dangerous to the consumer of the product and obviously the detection of such is an important part of quality control. The present embodiment provides a way to detect metal objects whilst performing other quality control functions by way of the NQR scanning.

The solution to performing metal detection simultaneously with NQR scanning is complex, as a metal object when brought into the scanning volume of a resonant coil detunes it, because the field generated by the coil induces current flow upon the metal object, which generates an opposing field. This opposing field slightly lowers the field contained within the coil and thus lowers the inductance of the coil.

As the resonant frequency of a coil is inversely proportional to its inductance and capacitance, as shown in equation (4), a change in inductance will result in a change in the resonant frequency of the coil. This results in the coil requiring retuning to be back on resonance. This can be achieved by adding capacitance to the coil by switching relays.

$$\omega = 1/\mathrm{sqrt}(L \cdot C) \qquad (4)$$

where:
$\omega = 2\pi$ times the frequency
L=inductance of the coil
C=Capacitance of the resonant circuit.

By measuring the amount of capacitance required to retune the coil, it is possible to determine if the container contains metal. Such a system would not be suitable for detecting metal inside bottles with metal lids or blister packs, which are coated on one side by a layer of aluminium foil for obvious reasons, but is better suited to detecting metal objects inside fully plastic containers.

One requirement for the system, however, is that the Q of the coil needs to be at least 200, preferably 400, in magnitude for this system to function. This is because it is too difficult to see small metal objects in a low Q system as the frequency shift is too small to be seen.

Figure 26:
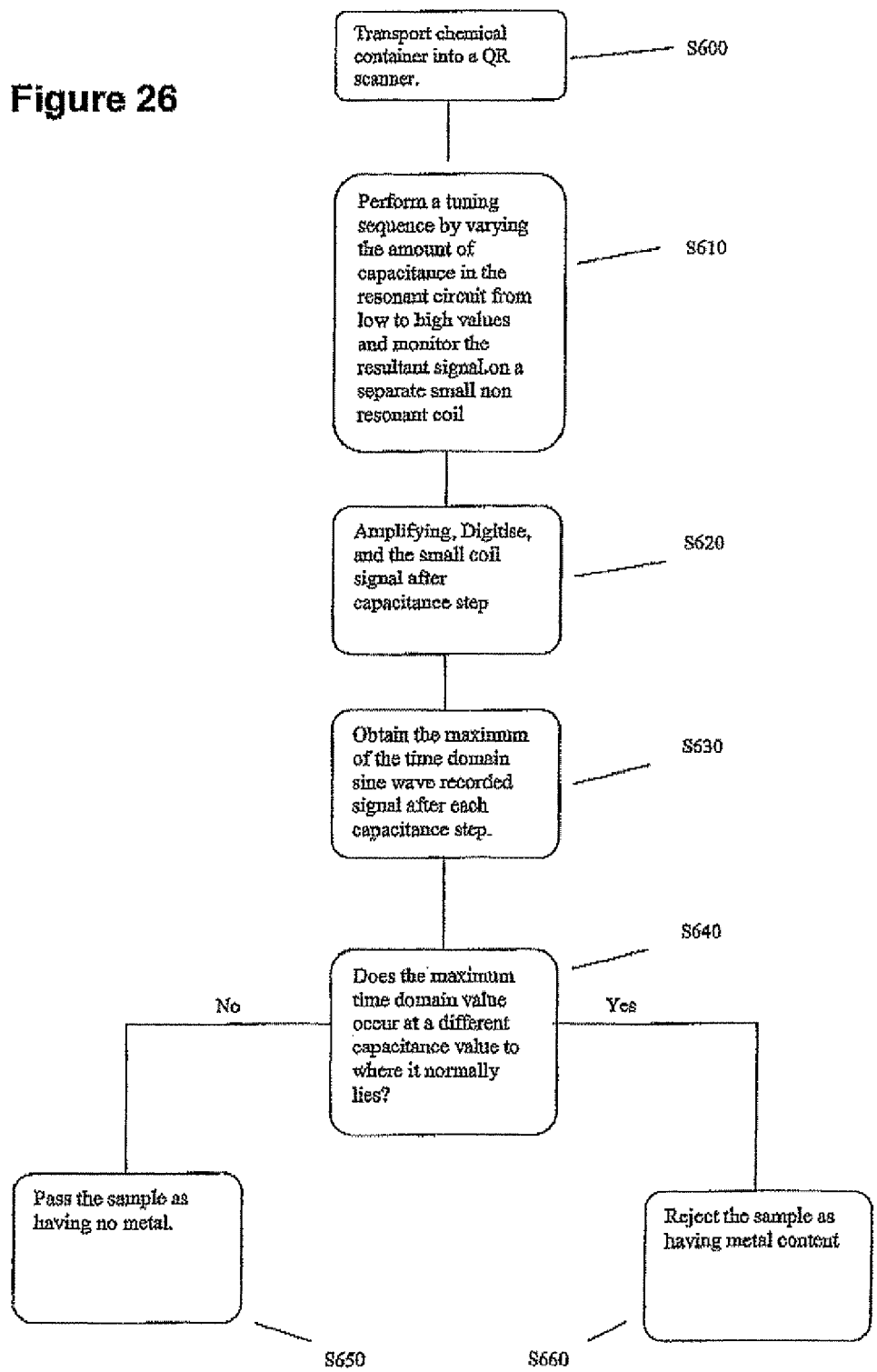
FIG. 26 is a flowchart showing the process followed for detecting metal as part of the quality control checking procedure performed in conjunction with NQR testing procedures in accordance with the fifteenth embodiment.

Hence, in the present embodiment, as shown in FIG. 26, a plastic container containing a chemical is moved into a QR scanner S600 and a tune sequence is performed S610. During the tune sequence the capacitance values are swept through a range of values and the signal is recorded upon another small coil located part way in between the main coil and the shield. The signal recorded on this small coil is amplified, mixed down to a lower frequency and sampled by an ADC S620. Here the maximum of this digital signal and the capacitance corresponding to this maximum signal is found S630. If this maximum capacitance value is significantly different from its normal value when no metal is present within the coil, then it is inferred that a piece of metal has been detected and an alarm is signalled or the sample is automatically rejected S660.

The sixteenth embodiment is directed towards a scanning system and method similar to the preceding embodiments, except that the detection station adopts a vertical orientation, as opposed to a horizontal orientation as described in the preceding embodiments.

Figure 27:
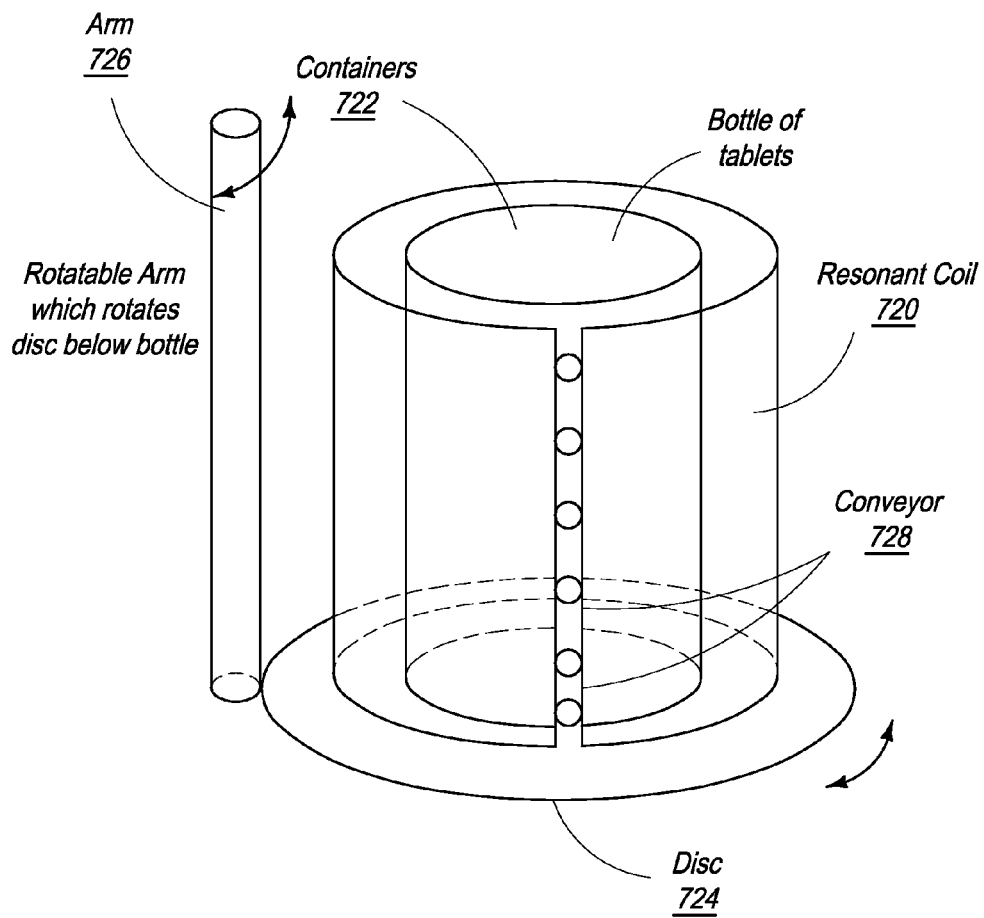
FIG. 27 is a schematic diagram showing a vertically oriented detection station in accordance with the sixteenth embodiment.
Figure 28:
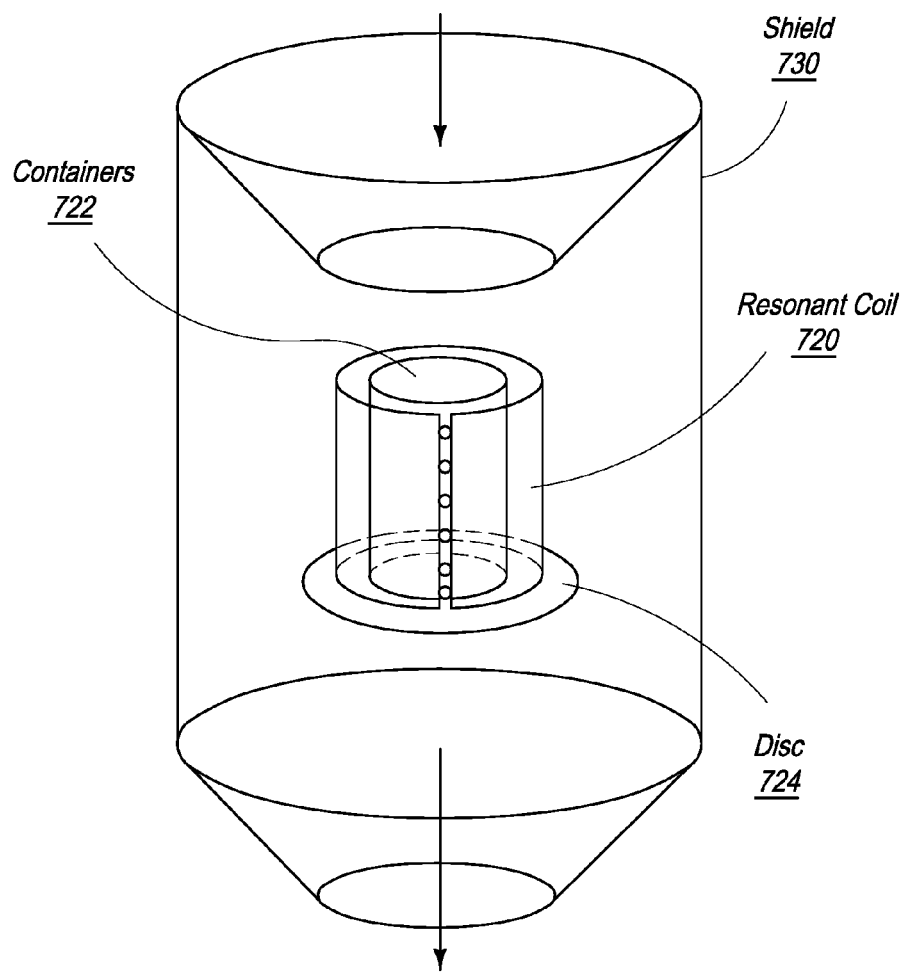
FIG. 28 is a schematic diagram showing the particular configuration of the electromagnetic shield used in conjunction with the coil and scanning chamber of the detection station shown in FIG. 27.

As shown in FIGS. 27 and 28, a cylindrical resonant coil 720 circumscribes a scanning chamber for receiving and dispensing containers 722 of a dosed amount of pharmaceutical to be checked for quality control purposes. A rotatable disc 724 is disposed beneath the coil 720, and is driven by a rotatable arm 726 into one position that retains a container with the chamber for NQR testing purposes, and into another position that permits the container to fall through and be discharged from the chamber under gravity.

The conveyor design accordingly is adapted to comprise an inlet delivery conveyor to deliver containers into the scanning chamber from above the coil, and a discharge receiving conveyor to receive containers discharged from the scanning chamber below the coil.

As shown in FIG. 28, the electromagnetic shield 730 is conically shaped at either end to function additionally as a funnel to facilitate guiding the passage of containers 722 both into and out of the scanning chamber as shown by the arrows.

The preceding embodiments are all directed towards fixed frequency in line or at line systems in situ to check the substance produced for quality assurance or quality control purposes. As well as being in line, the best mode can also be implemented through a stand alone QR spectrometer. Such instrumentation would be used for checking the shelf life-times of pharmaceutical products or at line/off line analyses. Such instrumentation would consist of.

Accordingly, the seventeenth embodiment is directed towards a portable QR system for quality control of on-shelf materials essentially comprising the same instrumentation components of the preceding embodiments as referred to above, namely a computer, pulse programmer, coil, power amplifier, receiver subsystem, shield, Q switch, all mounted within a self-contained housing located on a cart with caster wheels.

The cart is particularly dimensioned to fit between aisles or racks in a storage area, so it is relatively narrow, being less than 600 mm wide. The height of table top of the cart would ideally be matched to normal table height for testing purposes. The cart has a shelf built in for work space, so the operator can place samples thereon ready for testing.

The coil head is detachable from the main spectrometer and utilises plug in heads suitable for handling different package shapes or for analysing different types of material. In the case of the latter, the coils are pretuned by incorporating specific capacitors set to tune the coil to a particular frequency. Thus different coil heads incorporate different values of capacitor to tune to different frequencies, making it easier to switch from analysing one substance, to analysing another.

As described in certain of the preceding embodiments, the heads are adapted with guides so that the items for testing are always positioned and orientated the same relative to the coil head. Further, suitable means are provided for dispensing a package into the scanning head using an automatic feed that pipelines the articles, for instance in a tube.

Typically, very small samples are grouped together in lots, say of 5 or 10, for insertion into the probe as one unit. Again some kind of delivery means—a slotted tray with 5 or 10 bays, for example—is used for this purpose. This would improve throughput but loses the ability to scan individual items. Accordingly it would be applicable for very small packages and where the expected failure rate is low.

The embodiment of a portable QR system has several advantages. These include:

- The ability to preload a series of QA batch tests for one or more specimens with the ability to switch with single keystroke between one test and another as different types of items are pulled from the shelf. That is, the system would be flexible enough to test a run of one drug and then at the flick of a switch or keystroke, change to another species.
- Incorporate barcode scanning at the detection head or as part of the system on the cart so that each item is uniquely identified and reconciled with the QR test results,
- Overall scan times are shortened (cf. the full analytical testing) to maximise throughput.
- Simple alarm 'pass/fail' alert to operator based on preset test limits. The screen GUI is hidden or simplified. If the sample purity or concentration falls outside a predetermined limit, the result will be 'fail'.
- As there is an issue of threshold setting for determining detection rates, the threshold setting for the alarm is preset for a given high detection rate and the operator made aware of this so that there would be only a very small number of items that would give a false reading.
- Items that register as 'fail' on the test may be put aside and re-tested later—again using the same apparatus and as part of the same job—but with a more stringent test.
- The pulse sequences used for testing are sufficiently robust against metal in the bubble/blister packs and foil seals in the case of bottles. This means having a good rejection of magneto acoustic (MA) emissions. Thus coil and field alignment are adapted to minimise the effects of metal.

It should also be appreciated that various alternative embodiments of a portable QR system than the present embodiment provision of a cart on casters, can be provided. Moreover, in other embodiments, the portable QR system is embodied in a motorised buggy form, having its own battery for drive, as well for pulsing the QR signals. In further embodiments, the QR system is reduced down to a small electronics pack having a handheld wand that is positioned next to the pharmaceutical of interest.

At present it is very difficult to determine the resonant frequencies and other parameters of QR compounds. This is because computer programs designed for this purpose can only predict the resonant frequency to within 20% at best. For a 1 MHz frequency line this equates to a 200 kHz frequency range over which the search has to take place. Additional problems occur because relaxation times of the quadrupolar nuclei are also unknown and this makes pulse sequence selection very difficult. If the line is also weak it can take a long time to find the line and then find the optimum pulse sequence for the substance.

When analysing pharmaceutical compounds, it is expected that many, if not all, of these compounds will be newly discovered compounds and NQR information about these compounds will not be known. The pharmaceutical companies involved in manufacturing these compounds are not interested in consuming time and resources searching for these parameters. Hence, there is a need for an automated system for determining the NQR parameters and this needs to be done relatively quickly without the operator being required expend a lot of effort.

Figure 29:
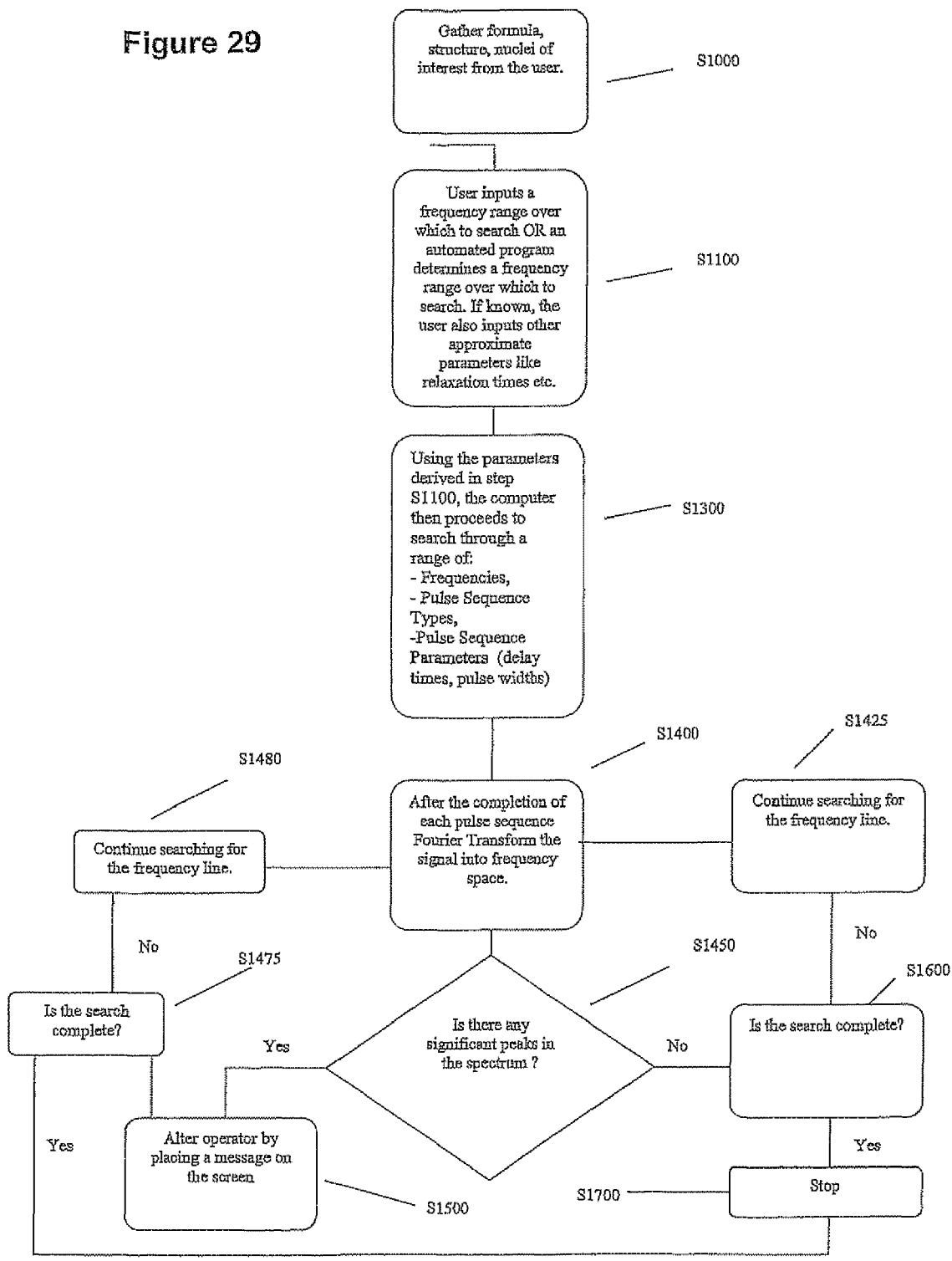
FIG. 29 is flowchart showing the process followed for automatically determining parameters associated with quadrupolar nuclei.

Hence, in the eighteenth embodiment, an automated method for determining parameters associated with quadrupolar nuclei is provided. Such a system negates the need for extremely tedious time consuming manual searching for frequency lines. As shown in FIG. 29, the method involves the following steps. In step 1000 the user is prompted for the formula, structure and the nuclei of interest. Knowledge about the structure and the nuclei of interest is important because the bond strengths dramatically affect the NQR frequency. In step 1100 the user inputs the frequency range over which to search or the computer automatically determines the frequency range. If known the user inputs the approximate relaxation times and pulse sequence parameters. In some cases the similarity of some compounds to others will mean that the user may be able to make an estimate of these parameters based upon previous results. In step 1300, using the parameters from step 1100, the computer proceeds to search for the unknown frequency line by building and transmitting a variety of pulse sequences to the transmit coil. Prior to executing this step the user would also obviously place the sample within the NQR coil.

Steady state type sequences are typically used with substances which have a short $T_1$ relaxation time. If the $T_1$ relaxation time is short this means that the pulse sequence can be repeated almost immediately. If however the $T_1$ is long (>0.2 sec), then a spin echo sequence will be needed to be used and there will need to be a delay of at least 1 or more seconds between pulse sequences. Hence, during step 1300, if the user doesn't know the approximate relaxation times, the computer begins with the fast steady state type sequences assuming that the $T_1$ relaxation time is short. Only after if it has exhausted all possible steady type sequences and is unable to find any resonance lines, does it begin to trial the slower spin echo type sequences.

During the searching for resonant frequency lines, the computer applies pulse sequences within which the frequency, pulse sequence type, and pulse sequence parameters (such as delay times and pulse widths) are varied. After each pulse sequence has executed, the resultant signal is transformed into frequency space. If any of the peaks are above the noise level in the spectrum, then they are displayed on the computer's screen. At this point the search may cease or it may continue searching for further lines in the same vicinity of the frequency spectrum.

Throughout the entire process the user is able to abort the search or stop and restart the search in case there are power failures. To facilitate this after each pulse sequence has been completed the computer saves enough information for it restart at the same point in the search.

At the end of the search, if successful, the operator should have results of the search displayed on the screen and saved to the computer's memory. The information that will be shown on screen will include the resonant frequency, pulse sequence type and pulse sequence parameters used to obtain the result. This enables the operator to reconstruct the pulse sequence and fine tune the pulse sequence parameters manually. This entire process saves the operator many hours of work, as it is envisaged that the machine could be searching for many days to find resonant lines.

Typical laboratory or field NQR measurements require a high Q coil and a high transmit power to achieve reliable detection because of the relatively weak nature of the NQR signal. The coil's high Q limits the bandwidth over which the frequency spectrum is irradiated, which results in typically only one or at most two NQR frequency lines that can be stimulated at once. This fact limits the searching for many known and unknown pharmaceutical lines simultaneously.

One technique which can overcome this problem is NQR stochastic resonance. This technique involves using low Q and a low power system to transmit a pseudo random train of pulses which can irradiate many frequency lines across a wide range of frequencies.

NQR stochastic resonance involves four main steps:
(i) Transmission of a pseudo random or truly random pulse sequence;
(ii) Detecting the NQR signal while the pulse sequence is being applied;
(iii) Gross correlating the NQR signal against the random or pseudo random pulse sequence, thereby generating a free induction decay (FID) or an echo;
(iv) Transforming the FID or echo derived in step (iii) into frequency space to determine if any peaks are present, which indicates the presence of a substance.

In step (i), the pulse sequence has constant pulse width and pulse spacing, but the phase of the pulses and the amplitudes are either fixed or vary truly randomly or pseudo randomly throughout the pulse sequence's operation. Because of this random nature of the phase, the pulse sequence looks like noise and hence stochastic resonance is sometimes called noise excitation. The flip angles generated by the pulses are much smaller than those typically observed elsewhere and range from 0° to 5°. Normally after each pulse, the signal acquisitions are cumulatively added together to form a single array. However in stochastic resonance the received signal is just accumulated into one long array and the acquisitions are not added together but placed side by side. Once the pulse sequence has been completed, then the accumulated army of NQR signals are cross correlated against the random or pseudo random train to produce a FID or echo. Once the FID or echo has been generated it is simple matter to Fourier transform the FID or echo generating peaks in frequency space.

In the case of pharmaceutical analysis additional steps are added to the above procedure:
(i) Determine the nature of the peaks that lie in the frequency spectrum. To be classed as a peak, the amplitude of the peak must lie a certain distance above the noise level in the frequency spectrum, typically 2 or three times.
(ii) The peaks in the frequency spectrum are then examined to determine if they lie at the frequency expected for any desired or undesired compounds.
(iii) If the peaks lie at a desired compound frequency then they are checked against a threshold. This threshold could correspond to the amount of substance in the container.
(iv) If the peaks lie at a point corresponding to an undesired compound, then they are checked against another separate threshold which is the level at which impurities are no longer tolerated. If the impurity peak lies above this threshold then the sample is rejected.
(v) If the peak is found to be of an unknown origin then it is flagged to the operator as such. Depending upon the operator, the sample can be rejected or not rejected on the basis of this unknown peak.

Hence in a nineteenth embodiment, a sample is brought into an NQR coil (ST190 in FIG. 30). Here the sample is irradiated with a random or pseudorandom train of pulses ST100 during which time the NQR response is also collected ST110. The train of pulses is accumulated into one array x(t) and the NQR response is accumulated into another array y(t). These two arrays are then cross correlated against each other ST120. The result of this cross correlation is an FID or an echo ST130. This FID or echo is then Fourier transformed into frequency space, where if any peaks are found, they are further examined. If the peak is an unknown peak, then the operator is informed ST150. If the peak is a desired peak ST100, then the peak is compared to a threshold ST200 to determine if there is the required amount of sample present in the container. If there isn't the sample is rejected ST220, otherwise the sample passes quality control ST210. If an undesired peak is found it is compared against another threshold ST190. This threshold represents the maximum allowed amount of the contaminant. If the undesired peak lies above this threshold, the sample is rejected ST220, otherwise the sample is passed ST230 as having satisfied quality control. In the case where the amount is correct and the contaminant peak is too large, the sample is automatically rejected.

In a variation of this embodiment, rather than checking the peak height, the widths are checked as per earlier embodiment to check the sample purity.

Using NQR in pharmaceutical analysis for, inter alia, quality control has several advantages.

It can by used in-line and in real time in conjunction with the manufacturing process.

It is non-evasive and thus non-destructive of the actual packaged substances, which if meeting quality standards, can continue to be processed for batch packaging and consignment.

It is highly specific and suffers from virtually no interference, whereas NMR, for example suffers interference from binders, plastics etc making spectral interpretation difficult.

It is far quicker than NMR, for example, where NMR spectra can take overnight runs to obtain, whereas NQR can be achieved in less than a minute or even seconds.

It can determine which polymorphic type of chemical is present (a requirement in the USA).

It can determine if the right chemical has been manufactured.

It can determine the amount of chemical in a sample, preventing overdoses or underdoses, incorrect number of tablets in a container etc.

It can be applied throughout the manufacturing process to prevent the wrong chemical being manufactured at any particular stage, including using the wrong inputs.

It requires no magnet, reducing cost & weight.

It can determine the purity and crystallinity of the sample via line widths.

It can determine if a substance is a counterfeit or of low quality.

It can be used to monitor extremely large volumes, i.e. vats, because it requires no magnet.

It can look at individual tablets to determine if they contain the right chemical by the use of PE methods.

Observed NQR frequencies can determine if an unknown or unwanted material is present—this might be important for poisonous drugs preventing expensive litigation.

The QR itself can be used as metal detector or a metal detector could be added to prevent metal entering the human body.

It should be appreciated that the scope of the present invention is not limited to the specific embodiments described herein. In particular, the invention is not limited to performing quality control of pharmaceuticals in a production environment. It has equal utility for quality control in other industries where a product including quadrupolar nuclei is produced, such as may arise in the chemical/plastics, cosmetics and foodstuff industries. For instance, quadrupolar nuclei such as $^{25}$Mg, $^{27}$Al, $^{79}$Br, $^{127}$I and $^{209}$Bi are often found in cosmetics where high standards of purity and reliability are equally desirable. Further, the invention can also be applied to quality assurance/quality control (QA/QC) operations in the mining industry.

The invention claimed is:

1. A method for analyzing polymorphic forms and concentrations of a polymorphic chemical substance containing quadrupolar nuclei to determine at least one measurable characteristic of the polymorphic chemical substance selected from the group comprising:
   a) an amount of a certain chemical in the polymorphic chemical substance;
   b) a purity of the polymorphic chemical substance;
   c) an identification of a particular polymorphic form of the polymorphic chemical substance;
   d) a temperature of the polymorphic chemical substance; and
   e) a frequency of the polymorphic chemical substance;
   wherein the determination comprises:
      irradiating the polymorphic chemical substance with RF energy in a prescribed manner to stimulate nuclear quadrupole resonance (NQR) of certain quadrupolar nuclei within the polymorphic chemical substance;
      receiving and processing a signal emitted from said polymorphic chemical substance in close association with the irradiating to isolate an NQR signal therefrom;
      analyzing said NQR signal to obtain said at least one measurable characteristic of the polymorphic chemical substance;
      providing an output indicative of said at least one measurable characteristic for analytical purposes; and
   using said obtained NQR signal to differentiate between different polymorphic forms and concentrations of the polymorphic chemical substance.

2. A method as claimed in claim 1, wherein information or data gathered during the analyzing process is automatically stored for future use.

3. A method as claimed in claim 1, wherein the prescribed manner comprises using a pulse sequence comprising a long multiple pulse echo train with phase cycling.

4. The method of claim 3, comprising adjusting a frequency of the pulse sequence by measuring the temperature and looking up a table or calculating the quadrupole resonance frequency that should be used at the measured temperature, subsequently using the known temperature-frequency relationship for a NQR line of a particular substance of interest, and then adjusting a transmit frequency to this value.

5. The method of claim 4, comprising correcting for the effects of increasing signal strength at lower temperatures by normalizing recorded signal strengths against their recorded temperature.

6. The method of claim 5, comprising using a predetermined relationship between signal intensity and temperature to calculate a temperature multiplier.

7. The method of claim 1, comprising measuring linewidth to identify chemicals having poor crystallinity or impurities, the method further comprising:
   (i) Determining a temperature of an environment within which said polymorphic chemical substance is located;
   (ii) Calibrating a quadrupole (QR) coil for irradiating the polymorphic chemical substance;
   (iii) Determining the temperature of the environment again;
   (iv) Measuring a QR line-width of the polymorphic chemical substance using a reproducible technique; and
   (v) Determining whether the line-width within a range of values for a required level of crystallinity.

8. The method of claim 1, using nuclear quadrupole coupling constant (NQCC) and asymmetry parameters to determine which chemicals are present in the polymorphic chemical substance present within a container, comprising:
   (i) Predetermining frequencies at which NQR frequency lines of desired and undesired compounds will occur, and determining relative signal strengths of each individual line at these frequency lines;
   (ii) Predetermining which pulse sequence and pulse sequence parameters should be used to detect said lines;
   (iii) Measuring a temperature of an environment within which said polymorphic chemical substance is located;
   (iv) Calibrating the expected relative signal strengths of the desired/undesired chemicals in a verified sample;
   (v) Measuring peak heights of two of frequencies for at least one chemical in the polymorphic chemical substance;
   (vi) Determining the NQCC and asymmetry parameters from the measured frequencies;
   (vii) Determining if the NQCC and asymmetry parameters match corresponding values for the desired compounds or undesired compounds; and
   (viii) On the basis of (vii), accepting or rejecting the container as having passed or not passed quality control requirements.

9. The method of claim 1 further comprising increasing the signal strength or decreasing waiting times in order to provide for faster measurement by
   applying a DC magnetic field to a sample of the polymorphic chemical substance, and
   adiabatically removing DC magnetic field from the sample;
   while applying a sequence of RF pulses to the sample, and detecting response signals from the sample.

10. The method of claim 1, comprising irradiating the polymorphic chemical substance with RF energy while concurrently receiving and processing a signal emitted from said polymorphic chemical substance in order to increase throughput.

11. The method of claim 1, comprising subjecting the polymorphic chemical substance to a metal detection device to detect metal contamination while concurrently detecting QR signals.

12. The method of claim 1, comprising automatically searching for chemicals within the polymorphic chemical substance, comprising:
   prompting for a formula, structure and nuclei of interest;
   inputting a frequency range;
   inputting approximate relaxation times and pulse sequence parameters; and
   searching for unknown frequency lines by building and transmitting a variety of pulse sequences to a coil adapted to transmit the RF energy.

13. The method of claim 1, further comprising using stochastic resonance to search for certain chemicals in the polymorphic chemical substance, comprising:
   (i) Applying a pseudo random or random pulse sequence to the polymorphic chemical substance;
   (ii) Detecting the NQR signal while the pulse sequence is being applied to the polymorphic chemical substance;
   (iii) Cross correlating the NQR signal against the random or pseudo random pulse sequence in order to generate a free induction decay (FID) or an echo; and
   (iv) Transforming the FID or echo derived in step (iii) into a frequency domain to determine if any peaks are present to indicate a presence of certain chemicals in the polymorphic chemical substance.

14. A method for analyzing polymorphic forms and concentrations of a chemical substance during production thereof to determine a polymorphic characteristic of the chemical substance indicative of a quality thereof, comprising:
irradiating the chemical substance with RF energy in a prescribed manner to stimulate nuclear quadrupole resonance (NQR) of certain nuclei within the chemical substance;
receiving and processing a signal emitted from said chemical substance to isolate an NQR signal therefrom;
analyzing said NQR signal to obtain an indication of the polymorphic characteristic of the chemical substance indicative of the quality thereof;
comparing said indication with prescribed reference parameters pertaining to that polymorphic characteristic; and
providing an output signal indicative of a result of said comparison to signify whether the chemical substance is in accord with quality requirements prescribed for that polymorphic characteristic and to differentiate between different forms of the chemical substance.

15. The method of claim 14, comprising calibrating the analyzing step to account for existing environmental conditions that could influence the accuracy of the indication of the polymorphic characteristic relative to the prescribed reference parameters.

16. The method of claim 15, wherein the calibrating step comprises measuring a temperature external of the chemical substance.

17. The method of claim 16, wherein the calibrating step comprises measuring an actual temperature of the chemical substance.

18. A system for analyzing polymorphic forms and concentrations of a polymorphic chemical substance to determine a polymorphic characteristic of the chemical substance, comprising:
a chamber configured for receiving and encompassing the chemical substance therein;
a probe containing a coil configured to irradiate said chamber with RF energy;
a conveyor to convey the chemical substance through said chamber;
generating and transmitting means to generate and transmit a signal in a prescribed manner to excite said probe so as to irradiate said chamber with RF energy in order to stimulate nuclear quadrupole resonance (NQR of certain nuclei within the chemical substance;
receiving and processing means to receive signals from said chamber in close association with said signal in order to isolate an NQR signal therefrom; and
analyse analyzing means to analyze said NQR signal in a manner so as to obtain a measure of the polymorphic characteristic of the chemical substance and to differentiate between different polymorphic forms and concentrations of the chemical substance.

19. The system of claim 18 further comprising three sets of orthogonal RF coils, and a program adapted to perform a three-frequency NQR analysis to obtain a frequency distribution of the polymorphic chemical substance being analyzed.

20. The system of claim 18, wherein said signal a phase-cycled multi-pulse sequence.

21. The system of claim 18, wherein said signal comprises an extended time echo sequence.

22. The system of claim 18, wherein the system is disposed in a side-line relationship to a main conveyor and operates in parallel with said main conveyor for conveying the chemical substance from said main conveyor to the conveyor of the system.

23. The system of claim 18, wherein the chamber and probe are arranged such that magnetic fields produced by the coil of the probe are orientated to be mostly parallel to any metal surfaces of a container containing the chemical substance.

24. The system of claim 18, wherein said system is self-contained and adapted to be portably disposed.

25. A method for analyzing polymorphic forms and concentrations of a polymorphic chemical substance to determine a polymorphic characteristic of the chemical substance, wherein said polymorphic characteristic is related to a quality of production of the polymorphic chemical substance; comprising:
(i) conveying the chemical substance into volume;
(ii) irradiating said volume with RF radiation in accordance with a prescribed pulse sequence at a prescribed frequency;
(iii) receiving signals from said chemical substance at said prescribed frequency;
(iv) processing said signals for nuclear quadrupole resonance (NQR) signals;
(v) determining quadrupole parameters from said NQR signals including any one of: line-width, frequency, peak height, impurity frequency; or any combination thereof;
(vi) determining a size of at least one of said quadrupole parameters;
(vii) comparing said size of at least one of said quadrupole parameters against at least one reference parameter to determine a qualitative measure of a polymorphic characteristic of said polymorphic chemical substance determinative from said at least one quadrupole parameter and to differentiate between different polymorphic forms and concentrations of the polymorphic chemical substance; and
(viii) generating a signal when if said qualitative measure differs beyond a threshold amount from said at least one reference parameter.

26. The method of claim 25, wherein said polymorphic characteristic comprises a chemical composition of the polymorphic chemical substance.

27. The method of claim 25, wherein said polymorphic characteristic comprises an amount of a particular polymorph chemical in the polymorphic chemical substance.

28. The method of claim 25, wherein said polymorphic characteristic comprises a purity of the polymorphic chemical substance.

* * * * *